United States Patent
Barone

(10) Patent No.: US 10,912,638 B2
(45) Date of Patent: Feb. 9, 2021

(54) PROSTHESIS FOR REPAIRING A BLOOD VESSEL AND METHOD

(71) Applicant: Hector Daniel Barone, Ciudad de Buenos Aires (AR)

(72) Inventor: Hector Daniel Barone, Ciudad de Buenos Aires (AR)

(*) Notice: Subject to any disclaimer, the term of this patent is extended or adjusted under 35 U.S.C. 154(b) by 517 days.

(21) Appl. No.: 15/398,384

(22) Filed: Jan. 4, 2017

(65) Prior Publication Data

US 2018/0116781 A1    May 3, 2018

(30) Foreign Application Priority Data

Oct. 28, 2016 (AR) .............................. P 20160103292

(51) Int. Cl.

| | |
|---|---|
| *A61F 2/07* | (2013.01) |
| *A61F 2/856* | (2013.01) |
| *A61F 2/82* | (2013.01) |
| *A61F 2/90* | (2013.01) |
| *A61F 2/06* | (2013.01) |
| *A61F 2/848* | (2013.01) |
| *A61F 2/958* | (2013.01) |
| *A61F 2/915* | (2013.01) |
| *A61F 2/966* | (2013.01) |

(52) U.S. Cl.
CPC .............. *A61F 2/07* (2013.01); *A61F 2/82* (2013.01); *A61F 2/848* (2013.01); *A61F 2/856* (2013.01); *A61F 2/90* (2013.01); *A61F 2/958* (2013.01); *A61F 2/915* (2013.01); *A61F 2/966* (2013.01); *A61F 2002/061* (2013.01); *A61F 2002/072* (2013.01); *A61F 2002/075* (2013.01); *A61F 2210/0076* (2013.01); *A61F 2230/001* (2013.01); *A61F 2250/0023* (2013.01); *A61F 2250/0069* (2013.01)

(58) Field of Classification Search
CPC ...... A61F 2/07; A61F 2/82; A61F 2210/0076; A61F 2002/061; A61F 2/95
See application file for complete search history.

(56) References Cited

U.S. PATENT DOCUMENTS

| | | | |
|---|---|---|---|
| 5,617,878 A * | 4/1997 | Taheri ................ | A61B 8/12 128/898 |
| 6,287,335 B1 * | 9/2001 | Drasler ................ | A61F 2/07 623/1.14 |
| 7,588,597 B2 | 9/2009 | Frid | |
| 8,100,960 B2 | 1/2012 | Bruszewski | |
| 2003/0074049 A1 * | 4/2003 | Hoganson ........... | A61F 2/07 623/1.13 |
| 2003/0204241 A1 * | 10/2003 | Dong ................... | A61F 2/07 623/1.13 |

(Continued)

*Primary Examiner* — Sarah W Aleman
(74) *Attorney, Agent, or Firm* — Norris McLaughlin, P.A.

(57) ABSTRACT

A prosthesis for repairing a blood vessel, wherein the prosthesis is inserted intraluminally and fixed in the vessel so as to isolate a diseased section thereof and maintain the flow of blood from the vessel to collateral vessels involved the diseased section, and the prosthesis comprises a stent support and a flexible fabric liner of woven material comprising a plurality of concentric layers, wherein each of said layers has a very open fabric web which allows the passage of blood flow through the layers during the installation or the prosthesis but which allows the sealing of layers once the prosthesis is installed. A method is also provided for safe installation of the prosthesis.

13 Claims, 14 Drawing Sheets

(56) References Cited

U.S. PATENT DOCUMENTS

| | | | |
|---|---|---|---|
| 2004/0059406 A1* | 3/2004 | Cully | A61F 2/07 623/1.11 |
| 2007/0208256 A1* | 9/2007 | Marilla | A61B 8/0833 600/467 |
| 2008/0108987 A1* | 5/2008 | Bruszewski | A61B 18/1492 606/32 |
| 2008/0208325 A1* | 8/2008 | Helmus | A61F 2/06 623/1.44 |
| 2010/0137969 A1* | 6/2010 | Rakos | A61F 2/06 623/1.13 |

* cited by examiner

PROSTHESIS FOR REPAIRING A BLOOD VESSEL AND METHOD

BACKGROUND OF THE INVENTION

1. Field of the Invention

The present invention relates to a prosthesis for repairing blood vessels having a diseased section involving collateral blood vessels and it preferably relates to a prosthesis for the treatment of aneurysms and/or aortic dissections for the intraluminal repair of the diseased section of the aorta, with the aorta involving collateral arteries such as the brachiocephalic trunk, the left carotid artery, the left subclavian artery, the celiac trunk, the superior mesenteric artery and/or the renal arteries. The perfusion of these arteries is vital and therefore the perfusion must be maintained not only during the time it takes to install the prosthesis but also once the prosthesis has been installed because any occlusion of these arteries is incompatible with the life of the patient bearing the lesion.

While the following description will particularly refer to an aortic prosthesis, it should be understood that said prosthesis is applicable to the repair or treatment of any blood vessel where one or more collateral vessels or arteries are involved. Reference to the aorta will be made because it is the vessel whose disease is more frequent.

2. Description of the Prior Art

When a blood vessel, such as an artery, has a diseased section with probability of damage or rupture, it can be repaired by an intraluminally implanted prosthesis. However, when this section involves one or more collateral vessels, i.e. collateral arteries, installation of such prosthesis should take into account not to temporarily, and still less, permanently, occlude a vital collateral artery. The aorta is the vessel with the highest incidence of this type of lesions.

The aorta is the main trunk of the arterial system, starting from the heart and extending down through the thorax and through the abdomen dividing into two iliac arteries. Among lesions that most affect the aorta, there are dissections and aneurysms. Both pathologies should be treated to prevent aortic rupture that would result in fatal hemorrhages in a very short time. This generally leads to the death of the individual suffering from said lesion.

As a result of the foregoing, a variety of intraluminal endoprosthesis have been developed that have made it possible to treat aneurysms and aortic dissections, thus avoiding conventional surgeries or open surgeries, and more particularly, avoiding postoperative symptoms caused by these surgical practices. When implanting a prosthesis of this type inside the aorta to isolate the diseased portion, it must be taken into account that there are several arteries that should not be obstructed when expanding and installing the prosthesis. To ensure that these arteries maintain their normal perfusion, several prostheses have been developed, among which there are the so-called fenestrated, which have perforations or places to be perforated. Some of these prosthesis are called branched, which have sleeves that are connected by means of bridges or branches to collateral arteries, to ensure continuity of blood flow through arteries. However, such sites already open or designed to be perforated should be provided at precise locations of the prosthesis to exactly match the entries or ostia of those arteries when the prosthesis is expanded and anchored. This problem, as it will be seen from the various prior art documents to which reference will be made, has not been satisfactorily resolved yet.

U.S. Pat. No. 7,588,597 to Noureddine discloses a luminal endoprosthesis comprising a braided or meshed support which includes a plurality of layers of biocompatible metal wires which are interlaced, wherein each of said layers is comprised of two folds or wires, which are dextrorotatory and levorotatory respectively, and which are interlaced to form a lattice or net. A plurality of wires of a given layer are integrated in the lattice or net of at least one of the adjacent layers, the plurality of layers providing an endoprosthesis with a side wall having a porosity capable of transforming a hemodynamic convection flow through the wall into a diffusion flow. Then, the idea of Nouredinne is that the blood flow passes through the metal mesh in those places where there is a leakage of flow and this happens in front of collateral arteries, that is to say inlets or ostia of such arteries.

Patent to Noureddine describes that the typical deformation of coated prostheses to prevent leakage leads to gradual occurrence of leakage between the endoprosthesis and the wall of the vessel. Consequently, the aneurysmal sac is pressurized again and the implanted prosthesis stops preventing rupture of the aneurism. Even when Nouredinne recognizes the problem of leakage to the aneurysmal sac, his proposed structure does not solve this problem because the metal mesh of the prosthesis, which allows the blood to pass through the ostia, does not have the means to perfectly seal around the ostia of the collateral arteries involved so that the flow passing through that is directed towards said arteries, crossing the mesh, is also directed to the inside of the aneurysm sac by means of which it will remain pressurized. That is, Noureddine has failed to isolate the aneurysm from the bloodstream.

U.S. Pat. No. 8,100,960 to Bruszewski discloses "bloused" graft stent and a fenestration method, wherein said stent comprises a proximal section, a distal section and a "bloused" section which is disposed between said proximal and distal sections and which is connected thereto by respective sutures. The Bruszewski stent as designed to anchor the proximal section above the arteries and thus arranging the "bloused" section in front of the respective ostia of said arteries. Bruszewski suggests that if a "bloused" section is located exactly in front of the ostium of a collateral artery, then, because of the difference in pressure between the aorta and the artery, for example the renal artery, there occurs "suction" of the "bloused" section so that a "pocket" is formed within the renal artery. Said pocket will later be fenestrated in order to generate an opening or window that allows circulation of blood flow. The fenestration method is carried out by the insertion of a piercing device whose tip pierces or perforates the pocket. Both the "bloused" section and the tip of the piercing device should carry radiopaque markers to facilitate the implantation and fenestration process. The Bruszewski's endoprosthesis appears to allow the aneurysm to be isolated. However, Bruszewski's endoprosthesis has the disadvantage that the window formed by puncture on the "bloused" section is a windows that remains open without any sealing against the wall of the aneurysm or aorta allowing not only the passage of blood towards the artery but also blood leakage between the wall of the prosthesis and the wall of the aorta around the ostium. All this would occur as long as the mesh of the bloused section in intimate contact with the ostium of the artery. Although Bruszewsky's FIG. 6 illustrates the cut edges of the prosthesis as sealing the periphery of the ostium, this does not happen in reality because nothing holds the edge of the window to the ostium and the typical pulsatile flow of blood will unfailingly generate leakages the edge and the wall of the ostium and the aorta. In other words, the edge of the perforated window has no seals or anchor on the wall of the artery to be connected. It should further be considered that the bloused section should be designed and arranged precisely in the prosthesis so that the section matches the opposite ostia, but not aligned, of the collateral arteries. The bloused section must necessarily have radiopaque markers to guarantee precisely locating the same opposite, in front of, the ostia. This is added to the fact that while positioning the prosthesis in the artery and arranging the bloused section in front of the ostia involved, it will not be possible to have the angiographic visualization of the precise location of arteries to be connected because the wall of the prosthesis will not al low circulation of blood with contrast liquid through the mesh towards the artery. Additionally, Bruszewski does not anticipate that the diameter of the dilatation at collateral level is greater than the diameter of the prosthesis. If so, the bloused section could not be positioned within the ostia as illustrated, rendering the exclusion of aneurysm unfeasible after perforation of fabric, except that the perforation would be interconnected with a branch of the selected artery, however this is not foreseen in said document. Another disadvantage to consider that Bruszewski's prosthesis is made of a fabric that must have a closed web not to allow the passage of blood out of the prosthesis. This is why the bloused section should be punctured, i.e. cut with a cutting or sharp instrument to open the passage of blood to the arteries. In that cut or puncture, no calculation errors are foreseen in the perforation of the fabric, which, if made outside the ostium, would cause an arterial rupture or damage to the wall of the aorta. As said before, this is because it is not possible to see the artery if there is no blood flow that carries contrast medium to the artery to see its location by angiography techniques.

On the other hand, US Patent No. 2004/0059406 to Cully et al. discloses an implantable prosthesis having at least one distinct perforable sector, i.e. for fenestration, which incorporates a "patch" having a window delimited by a frame, capable of being punctured or punched through which a wire guide can be passed with an expandable balloon catheter. The patch comprises a sandwich structure in which the frame or silhouette is surrounded by a layer of implantable polymer material and the window being completely covered by a barrier of breakable material. As can be seen in the figures of patent to Cully et al., the window is traversed by the expandable balloon catheter and is opened by inflating the balloon. When the balloon deflates, the window is deformed allowing the passage of blood flow. Also, there is provided a prosthesis to ensure that the deformed window is kept open without obstructing the blood flow passage. Although the breakable barrier allows perforating and passing an expandable balloon to form a window in which an interconnecting branch or prosthesis may be connected to an involved artery, said breakable barrier is disposed at a preselected location to be matched with the ostium of the artery where the interconnecting prosthesis should be connected. As explained above in relation to other devices of the prior art, it is very difficult, if not impossible, during the implantation of an endoluminal prosthesis to arrange a portion or sector thereof in perfect matching with a collateral artery with which it is sought to establish a fluid connection. Still less, accurate positioning for simultaneous interconnection with four collateral arteries would be impossible. This is done by using radiopaque markers around the breakable material, which operate as contrast medium, to locate, during implantation, the exact location of the patch and its breakable material, by means of angiography. It is worth remembering again that once the prosthesis is expanded, the ostium of the artery to be connected is blocked by the wall of the prosthesis and as no blood circulates to the artery, two fundamental problems occur. One is that the artery can not remain for a long time without perfusion because the lack of blood supply to the organ fed by the artery would cause the organ to die and the other problem is that since there is no blood supply through the artery there is no way to send through it the necessary contrast liquid that allows to see the artery by means of the known angiographic techniques. If you do not have an accurate ostium location the tool that used to pierce the pierceable barrier material can pierce the wall of the aorta instead of exactly penetrating the ostium of the artery to connect.

These problems mentioned above have been considered in AR Patent Application No. P 20160101195 to the same inventor/applicant of the present invention, which discloses an aortic prosthesis for the treatment of abdominal aortic aneurysms, where the prosthesis is implanted intraluminally and comprises a main body made up of a backbone or support, stent, covered by a mesh having three sections with different degrees of porosity, an upper portion having a higher porosity, an intermediate one having intermediate porosity, and a lower one having the lowest porosity. The upper portion, with greater porosity, is intended to be secured firmly against the aortic wall, at the level of the renal arteries, through anchoring means. The intermediate portion must be arranged below the renal arteries and the lower portion is freely disposed at a position within the aneurysm and above the iliac arteries with which it will be connected by means of branches to exclude the aneurysm from circulation.

The correct operating condition of this prosthesis requires that the most open web be positioned outside the diseased section of the aorta and in close contact with the healthy wall of the aorta. The purpose of this web with arteries involved. Since, as it is said above, this section with greater porosity should only be positioned against the healthy wall of the aorta, said collateral arteries must necessarily be in said section of healthy wall. If the collateral arteries are within the diseased section, this endoprosthesis can not be successfully employed because the more porous web section would not seal by itself the flow therethrough even after reversing the patient's anti-coagulation state.

Additionally, the most porous web section must be interconnected with the corresponding collateral artery by means of an interconnecting branch, because although it has high porosity it would decrease the flow towards the collaterals over time and eventually, it would be a clot forming matrix that would generate a distal embolization towards kidneys.

In summary, the latter endoprosthesis requires an installation wherein said more porous web section is not positioned within a diseased section but in a healthy section of the aorta and for this, as in all other prior art cases mentioned above, contrast markers for its location during installation will be needed.

It would therefore be desirable to have a new prosthesis for the treatment of arterial lesions capable of being installed without worrying about the positioning of predetermined sections, sectors, blouses or patches that must be located matching collateral arteries to be interconnected within a diseased section of the artery, allowing the practitioner to position, expand and install the prosthesis throughout the diseased section even though these collateral arteries are covered by the endoprosthesis. Thus, the professional should only concentrate on positioning and anchoring the ends of the prosthesis beyond the diseased section, which is habitual and does not represent any difficulty in the practice of art.

SUMMARY OF THE INVENTION

It is therefore an object of the present invention to provide a prosthesis, preferably an aortic prosthesis, for the exclusion of any type of aortic aneurysm or dissection where there are collateral arteries involved, and which can be installed and implanted within the aorta without risk of damage or lack of perfusion for any of said collateral arteries that are in the area of the aorta to be repaired, neither during nor after its installation.

It is yet another object of the present invention to provide an aortic prosthesis for use in repairing aneurysms and thoracic and abdominal thoracic aortic dissections by inserting the prosthesis into the aorta to exclude the aneurysm or dissection from blood circulatory system, the prosthesis comprising a support and a liner of flexible fabric material defined by a plurality of layers, preferably at least two or three concentric layers which have webs, nets, or grids, open enough to allow blood perfusion to any collateral artery involved during the time for the installation and which also allow to be traversed, without rupture, for the installation of prostheses or branches of interconnection with said any artery, but the layers being combined so as to allow sealing of the wall of the aortic prosthesis, preventing the passage of blood through said wall, once said installation is finished.

It is a further object of the present invention to provide a prosthesis for repairing a blood vessel comprising a main prosthesis whose wall is formed by a plurality of layers of fabric, preferably at least two or three concentric layers each having, a fabric web which is sufficiently open to allow passage of blood flow without any inconvenience and the layers being arranged so that the wall formed therein has a combined web which allows said passage of blood during a controlled time.

It is a further object of the present invention to provide a main aortic prosthesis having at least three overlapping layers in such a way as to define flexible fabric mesh or web or liner that allows passage of blood flow during a controlled time, and that it further allows to be pierced by the piercing tip or end of a device to open a passage or channel without rupture of the web, fibers or fabric, to carry out the implantation of one or more interconnecting prostheses for interconnection with one or more respective collateral arteries through passages or channels formed in said web composed of said three layers.

It is yet another object of the present invention to provide a liner comprised of a plurality of layers, preferably at least three concentric layers of very open fabric web, which provides increased time in surgery to perform the implantation of a main aortic prosthesis with its interconnecting prostheses with collateral arteries involved.

It is still another object of the present invention to provide a prosthesis for repairing blood vessels, wherein the prosthesis is intraluminally inserted and fixed into one blood vessel of a patient, covering a diseased section of the vessel, with the blood vessel having collateral vessels the perfusion of which must be guaranteed during and after the implantation of the prosthesis, the prosthesis comprising:

a) a main prosthesis comprising:
i) a expandable support for firmly affixing into said blood vessel and along said diseased section, and ii) a liner made of a fabric material comprised of a plurality of concentric layers, wherein each layer provides a web that is open enough to allow the blood flow passing therethrough, and the layers are overlapped all together to form a wall of the main prosthesis defining labyrinthine interstices capable of being open during a controlled period of time for the installation and implantation of the main prosthesis, which interstices are sealed by the fibrin of the patient's blood after said period of time has elapsed, wherein said interstices formed by the web of each one of the overlapping layers are capable of being opened by a non cutting element passing through the interstices to form at least one passage through the wall formed by the plurality of concentric layers, and b) at least one interconnecting prosthesis for installation through said at least one passage through the wall formed by the plurality of concentric layers, with the interconnecting prosthesis being installed to seal into said at least one passage against said wall formed by the plurality of layers, and into and against a wall of one of the collateral vessels involved in the diseased section, the interconnecting prosthesis interconnecting an interior of the main prosthesis with said one of the collateral vessels.

It is another object of the present invention to provide a method for the implantation of a prosthesis for the repair of a patient's blood vessel involving collateral vessels, wherein the prosthesis comprises:

a) a main prosthesis comprising:
i) a expandable support for firmly affixing into said blood vessel and along said diseased section, and
ii) a liner made of a fabric material comprised of a plurality of concentric layers, wherein each layer provides a web that is open enough to allow the blood flow passing therethrough, and the layers are overlapped all together to form a wall of the main prosthesis defining labyrinthine interstices capable of being open during a controlled period of time for the installation and implantation of the main prosthesis, which interstices are sealed by the fibrin of the patient's blood after said period of time has elapsed, wherein said interstices formed by the web of each one of the overlapping layers are capable of being opened by a non cutting element passing through the interstices to form at least one passage through the wall formed by the plurality of concentric layers, and b) at least one interconnecting prosthesis for installation through said at least one passage through the wall formed by the plurality of concentric layers, with the interconnecting prosthesis being installed to seal into said at least one passage against said wall formed by the plurality of layers, and into and against a wall of one of the collateral vessels involved in the diseased section, the interconnecting prosthesis interconnecting an interior of the main prosthesis with said one of the collateral vessels, and wherein the method comprises the steps of:

installing said main prosthesis via endovascular way, using a first guide, in a blood vessel, with the prosthesis being positioned so as to extend along said diseased section of the blood vessel, wherein said collateral vessels, that must be connected, arise from said diseased section, and installing said at least one interconnecting prosthesis in any place of the wall of the main prosthesis that is detected that is in front of any of said collateral vessels to be connected, wherein a fluid communication is established between an interior of said main prosthesis and the connected collateral vessel.

It is a further object of the present invention to provide a method for the implantation of a prosthesis for the repair of a patient's blood vessel involving collateral vessels, wherein the prosthesis comprises:

a) a main prosthesis comprising:

i) a expandable support for firmly affixing into said blood vessel and along said diseased section, and ii) a liner made of a fabric material comprised of a plurality of concentric layers, extending, for example, around a geometrical longitudinal axis, wherein each layer provides a web that is open enough to allow the blood flow passing therethrough, and the layers are overlapped all together to form a wall of the main prosthesis defining labyrinthine interstices capable of being open during a controlled period of time for the installation and implantation of the main prosthesis, which interstices are sealed by the fibrin of the patient's blood after said period of time has elapsed, wherein said interstices formed by the web of each one of the overlapping layers are capable of being opened by a non cutting element passing through the interstices to form at least one passage through the wall formed by the plurality of concentric layers, and b) at least one interconnecting prosthesis for installation through said at least one passage through the wall formed by the plurality of concentric layers, with the interconnecting prosthesis being installed to seal into said at least one passage against said wall formed by the plurality of layers, and into and against a wall of one of the collateral vessels involved in the diseased section, the interconnecting prosthesis interconnecting an interior of the main prosthesis with said one of the collateral vessels, and wherein the method comprises the steps of:

installing said main prosthesis via endovascular way, using a first guide, in a blood vessel, with the prosthesis being positioned so as to extend along said diseased section of the blood vessel, wherein said collateral vessels, that must be connected, arise from said diseased section, advancing on said first guide a first introducer having a valve, a dilator and a retracting end, removing the dilator and said first guide and bending the retracting end of the first introducer to locate the retracting end in front of an ostium of a collateral vessel to be connected, which ostium is located on the other side of the wall of the main prosthesis, advancing a second straight tip guide into said first introducer and passing said second guide through said plurality of layers of the wall of the main prosthesis to form a passage through said wall, entering said second guide into said collateral vessel to be connected, introducing catheter balloon via said first introducer, with the catheter balloon being mounted on said second guide, and passing the catheter balloon through said passage through the wall of the main prosthesis, through interstices formed between webs of said plurality of layers and displacing strands or fibers of the webs, without cutting, breaking or tearing such fibers or strands, inflating said balloon to a diameter smaller than a diameter of the collateral vessel to be connected, so as to enlarge said passage from side to side of the wall of the main prosthesis, deflating and removing said catheter balloon, introducing along the first introducer, a second introducer with dilator, mounted on said second guide, passing the second introducer through said open passage in said plurality of layers forming said wall of the main prosthesis and positioning the second introducer with dilator within the collateral vessel to be connected, removing the dilator from the second introducer, introducing, into the second introducer and onto said second guide, an interconnecting prosthesis mounted on an expanding balloon, positioning the interconnecting prosthesis in the desired location, sliding the second introducer backwards and leaving the interconnecting prosthesis in position within said passage formed in the wall of the main prosthesis and into the collateral vessel to be connected, inflating the expanding balloon with the interconnecting prosthesis mounted thereon, deploying the interconnecting prosthesis, dilating said passage formed in said wall of the main prosthesis and impacting the interconnecting prosthesis within the collateral vessel to be connected, thus interconnecting the interior of the main prosthesis with the collateral vessel, deflating said expanding balloon, removing the expanding balloon from the second introducer, removing the second introducer, removing the second guide, positioning the first introducer in the desired position to connect another collateral vessel, and repeating the above steps for the connection of said other collateral vessel.

It is another object of the present invention to provide a method for the implantation of a prosthesis for the repair of a patient's blood vessel involving collateral vessels, wherein the prosthesis comprises:

a) a main prosthesis comprising:

i) a expandable support for firmly affixing into said blood vessel and along said diseased section, and ii) a liner made of a fabric material comprised of a plurality of concentric layers, extending, for example, around a geometrical longitudinal axis, wherein each layer provides a web that is open enough to allow the blood flow passing therethrough, and the layers are overlapped all together to form a wall of the main prosthesis defining labyrinthine interstices capable of being open during a controlled period of time for the installation and implantation of the main prosthesis, which interstices are sealed by the fibrin of the patient's blood after said period of time has elapsed, wherein said interstices formed by the web of each one of the overlapping layers are capable of being opened by a non cutting element passing through the interstices to form at least one passage through the wall formed by the plurality of concentric layers, and b) at least one interconnecting prosthesis for installation through said at least one passage through the wall formed by the plurality of concentric layers, with the interconnecting prosthesis being installed to seal into said at least one passage against said wall formed by the plurality of layers, and into and against a wall of one of the collateral vessels involved in the diseased section, the interconnecting prosthesis interconnecting an interior of the main prosthesis with said one of the collateral vessels, and wherein the method comprises the steps of:

installing said main prosthesis via endovascular way, using a first guide, in blood vessel, with the prosthesis being positioned so as to extend along said diseased section of the blood vessel, wherein said collateral vessels, that must be connected, arise from said diseased section, advancing on said first guide a first introducer having a valve, a dilator and a retracting end, removing the dilator and said first guide and bending the retracting end of the first introducer to locate the retracting end in front of an ostium of a collateral vessel to be connected, which ostium is located on the other side of the wall of the main prosthesis, advancing a second straight tip guide into said first introducer and passing said second guide through said plurality of layers of the wall of the main prosthesis to form a passage through said wall, entering said second guide into said collateral vessel to be connected, introducing along the first introducer, a second introducer with dilator, mounted on said second guide, passing the second introducer through said open passage in said plurality of layers forming said wall of the main prosthesis and positioning the second introducer with dilator within the collateral vessel to be connected, removing the dilator from the second introducer, introducing, into the second introducer and onto said second guide, an interconnecting prosthesis mounted on an expanding balloon, positioning the interconnecting prosthesis in the desired location, sliding the second introducer backwards and leaving the interconnecting prosthesis in position within said passage formed in the wall of the main prosthesis and into the collateral vessel to be connected, inflating the expanding balloon with the interconnecting prosthesis mounted thereon, deploying the interconnecting prosthesis, dilating said passage formed in said wall of the main prosthesis and impacting the interconnecting prosthesis within the collateral vessel to be connected, thus interconnecting the interior of the main prosthesis with the collateral vessel, deflating said expanding balloon, removing the expanding balloon from the second introducer, removing the second introducer, removing the second guide, positioning the first introducer in the desired position to connect another collateral vessel, and repeating the above steps for the connection of said other collateral vessel.

It is a further object of the present invention to provide a method for the implantation of a prosthesis for the repair of a patient's blood vessel involving collateral vessels, wherein the prosthesis comprises:

a) a main prosthesis comprising:

i) a expandable support for firmly affixing into said blood vessel and along said diseased section, and ii) a liner made of a fabric material comprised of a plurality of concentric layers, extending, for example, around a geometrical longitudinal axis, wherein each layer provides a web that is open enough to allow the blood flow passing therethrough, and the layers are overlapped all together to form a wall of the main prosthesis defining labyrinthine interstices capable of being open during a controlled period of time for the installation and implantation of the main prosthesis, which interstices are sealed by the fibrin of the patient's blood after said period of time has elapsed, wherein said interstices formed by the web of each one of the overlapping layers are capable of being opened by a non cutting element passing through the interstices to form at least one passage through the wall formed by the plurality of concentric layers, and b) at least one interconnecting prosthesis for installation through said at least one passage through the wall formed by the plurality of concentric layers, with the interconnecting prosthesis being installed to seal into said at least one passage against said wall formed by the plurality of layers, and into and against a wall of one of the collateral vessels involved in the diseased section, the interconnecting prosthesis interconnecting an interior of the main prosthesis with said one of the collateral vessels, and wherein the method comprises the steps of:

installing said main prosthesis via endovascular way, using a first guide, in a blood vessel, with the prosthesis being positioned so as to extend along said diseased section of the blood vessel, wherein said collateral vessels, that must be connected, arise from said diseased section, advancing on said first guide a first introducer having a valve, a dilator and a retracting end, removing the dilator and said first guide and bending the retracting end of the first introducer to locate the retracting end in front of an ostium of a collateral vessel to be connected, which ostium is located on the other side of the wall of the main prosthesis, introducing and advancing, along and inside said first introducer, a second introducer with dilator and, exerting a slight rotation on an axis of the second introducer and pushing forward, passing the second introducer through the plurality of layers forming the wall of the main prosthesis, to form a passage through this wall, and positioning the second introducer with dilator within the collateral vessel to be connected, positioning, through the dilator of the second introducer, a second guide within the collateral vessel to be connected, removing the dilator from the second introducer, introducing, into the second introducer and onto said second guide, an interconnecting prosthesis mounted on an expanding balloon, positioning the interconnecting prosthesis in the desired location, sliding the second introducer backwards and leaving the interconnecting prosthesis in position within said passage formed in the wall of the main prosthesis and into the collateral vessel to be connected, inflating the expanding balloon with the interconnecting prosthesis mounted thereon, deploying the interconnecting prosthesis, dilating said passage formed in said wall of the main prosthesis and impacting the interconnecting prosthesis within the collateral vessel to be connected, thus interconnecting the interior of the main prosthesis with the collateral vessel, deflating said expanding balloon, removing the expanding balloon from the second introducer, removing the second introducer, removing the second guide, positioning the first introducer in the desired position to connect another collateral vessel, and repeating the above steps for the connection of said other collateral vessel.

BRIEF DESCRIPTION OF THE DRAWINGS

The present invention illustrated by way of example in the following drawings wherein.

DESCRIPTION OF THE PREFERRED EMBODIMENTS

Referring now in detail to the figures, it is seen that the invention consists of a new aortic prosthesis for the treatment of aneurysms and/or dissections, which may be installed intraluminally within the aorta without risk of damage and undesired occlusion of any collateral artery involved in the aortic section to be repaired. The prosthesis of the invention comprises a main prosthesis to which one or more secondary or interconnecting prostheses can be easily connected, which are secured and sealed in the main aortic prosthesis passing through the wall of the prosthesis without breaking, cutting or tearing the fabric or any yarn of the layers of the prosthesis wall. These cuts and tears are unavoidable in the use of the aortic prostheses of the prior art. Distinct from that, the invention provides the formation of a passage, channel, aperture or window on the wall of the main prosthesis for the sealed connection of the interconnecting prosthesis to be implanted within the corresponding collateral artery to ensure the flow of blood from the aorta to the artery. It is pointed out that while in some figures there has been shown a prosthesis to be implanted in cases of thoracoabdominal aortic aneurysms, this does not imply that the invention is limited thereto, but that the prosthesis of the invention may be used in the ascending aorta, arch, and descending aorta.

Figure 1:
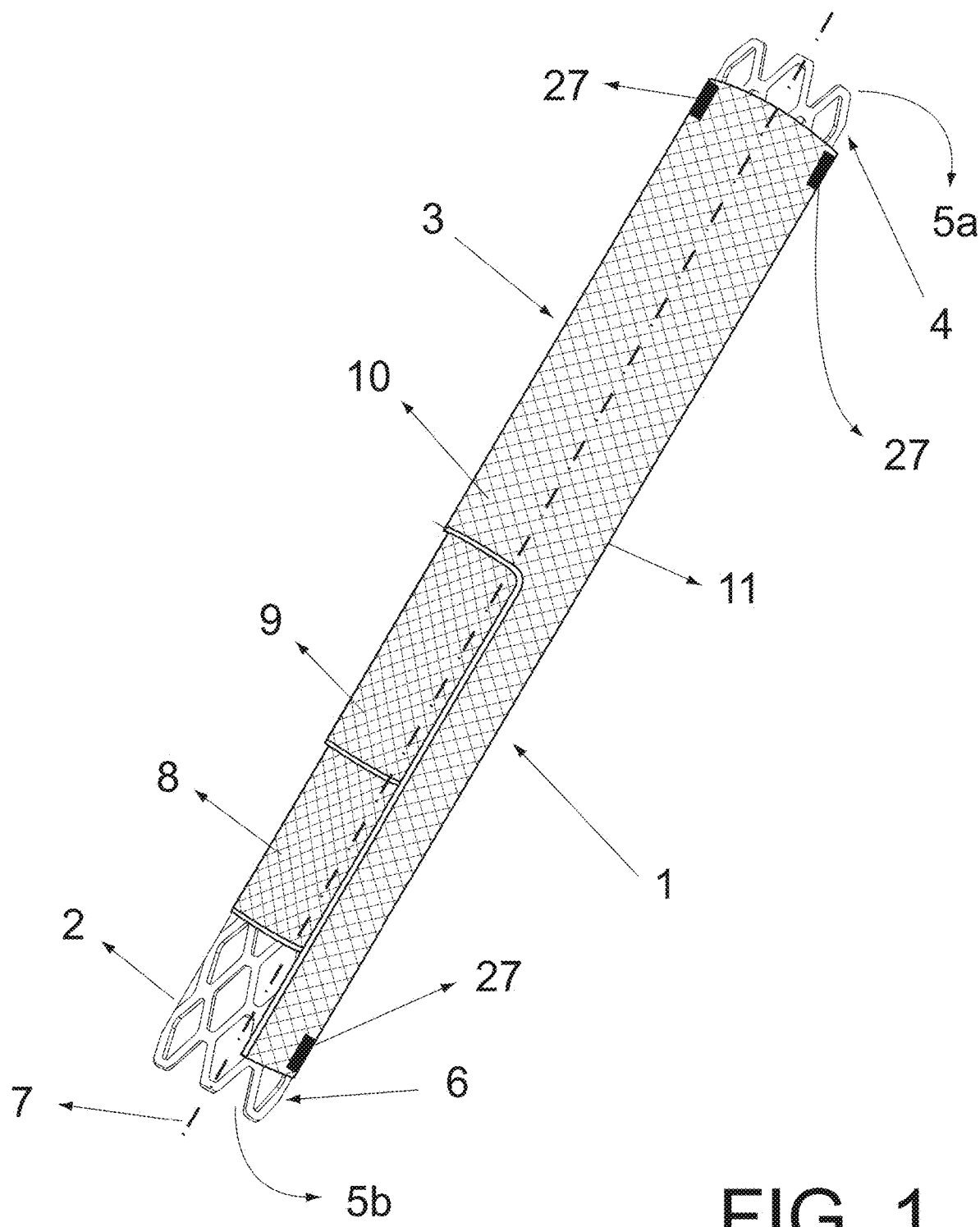
FIG. 1 shows a perspective and partial cross-sectional view of the main prosthesis comprising a plurality of layers made of very open mesh or web, in accordance with the present invention.
Figure 2:
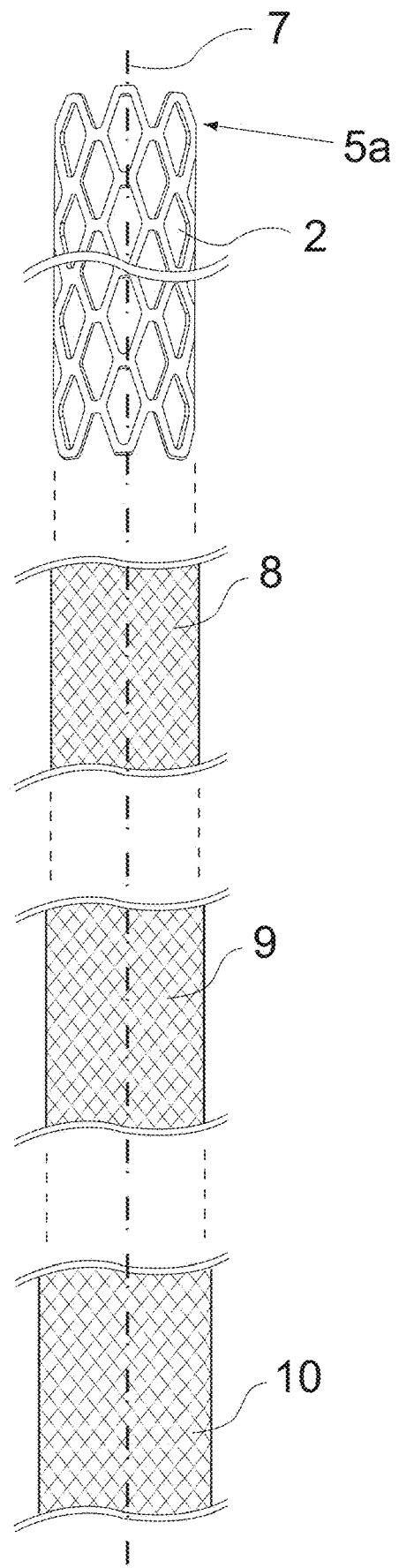
FIG. 2 shows an exploded view of the main prosthesis according to the present invention.
Figure 3:
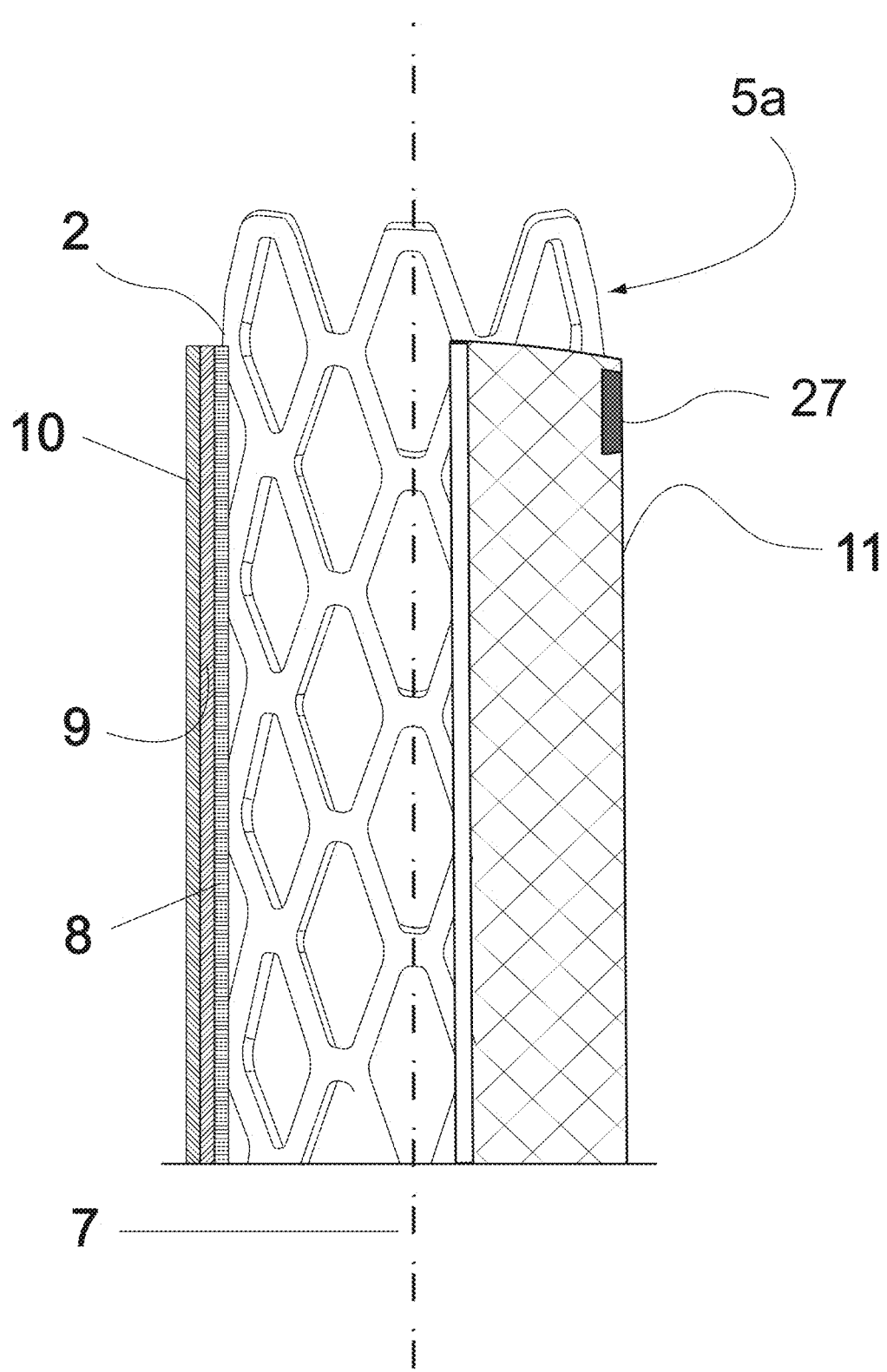
FIG. 3 shows a partial cross-sectional side view of the main prosthesis of the present invention.

According to the invention there is provided a novel aortic prosthesis formed by a main prosthesis, which is illustrated in FIG. 1, and is indicated by the general reference 1 and comprises a support 2 and a liner 3 of flexible or compliant cloth of woven material. Wherein said support 2 has a cylindrical structure which may comprise a stent or metal backbone which may be known, of the self-expandable or balloon-expandable type. Stent or support 2 extends along the entire main prosthesis 1 accompanying liner 3. Stents as anchoring means are well known and used in the field of the art of the invention and for such reasons no descriptive details about the same will be included. The stent has two ends, an upper 4 and a lower 6, and it optionally has both anchor portions 5a and 5b protruding beyond the edge of liner 3 to facilitate anchoring of the prosthesis to the aortic wall.

Figure 13:
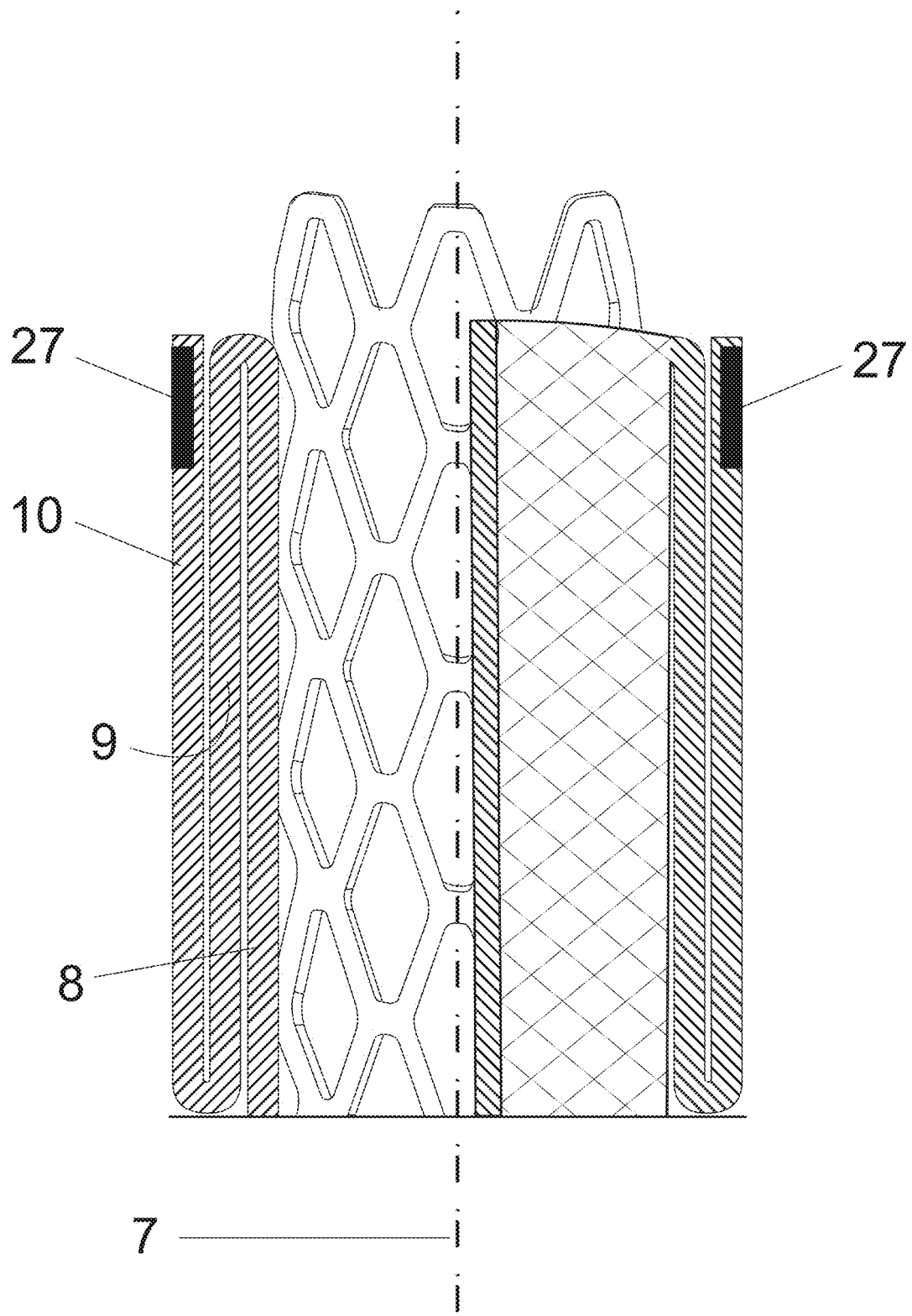
FIG. 13 is a longitudinal section and partly in cross-section view showing an alternate embodiment of the main aortic prosthesis consisting of three layers of fabric formed from a single tubular fabric invaginated in zig-zag shape.

On its turn, the woven fabric liner 3 has, in accordance with the invention, a novel shape comprising a plurality of layers, at least two, preferably at least three layers, arranged concentrically with respect to a longitudinal axis 7. In accordance with a preferred embodiment of the invention, said layers comprise an inner layer 8, an intermediate layer 9 and an outer layer 10 which overlap each other defining a wall or membrane 11 of the prosthesis. It should be noted that layers may be independent of each other and overlap so that the structural unity between them defining the prosthesis wall is achieved when the prosthesis is expanded with support or stent 2, to be anchored against the aortic wall. The layers may be separate layers and arranged one into the other as indicated, or they may be a single tubular fabric arranged in a zig-zag invaginated pattern to define three layers in the length of the prosthesis, as illustrated in FIG. 13. Whether the layers constitute separate fabrics or a unique zig-zag fabric, they may be attached to the stent or metal backbone 2 by known techniques and means, such as sutures, clips, and the like.

Also, each of inner 8, intermediate 9 and outer 10 layers comprises a fabric of any suitable type, for example weft and warp knitted fabric, knitted fabric, etc. The multiple layers forming the wall or membrane 11 may be of the same type of fabric or of different fabrics. According to the concepts of this invention, each layer, separately, has a fabric web sufficiently open as to allow passage of blood flow therethrough without any restriction. Thus, none of the layers forming the wall or membrane of the present aortic prosthesis could be employed in unitary or separate form to prevent passage of blood flow through the prosthesis and to form a matrix to fix the amount of fibrin of blood necessary to seal its pores once it is implanted and the anticoagulant treatment necessary in this type of procedures has been reversed. The seal, necessary to exclude the aneurysm or dissection, can only be obtained by combining said plurality of layers, for example the three layers 8, 9 and 10, which, according to the invention, work together. Thus, by working together they do something they could not do separately and that is to provide three-dimensional structure for the formation of a fibrin matrix that interconnects all the layers and seals the pores or interstices of this multilaminar structure of the wall.

"Sufficiently open web" of each layer is understood to mean the one whose porosity is such that its resistance to the passage of water therethrough is very low. The porosity of each layer may be the same or different, i.e. all layers may have the same or different webs; they may also have equal porosities or different porosities between layers. On the other hand, said wall formed by the plurality of layers 8, 9 and 10 could have an initial water porosity of more than 2500 cm$^3$/cm$^2$/minute when a conventional woven prosthesis has a porosity of between 50 and 200 cm3/cm2/minute.

More particularly, the layers of the main prosthesis of the invention are extremely thin and highly porous and form, in combination, a three-dimensional matrix or three-dimensional structure in which fibrin from the patient's blood will seal the pores only after a controlled time. For this to happen, it is necessary for the layers to be in intimate contact throughout their length, therefore the internal metal stent or backbone 2, being of the self-expanding type or being of the balloon-expandable type, must expand said layers during implantation, radially outwardly and maintain them in permanent tension and in intimate contact with each other. The fabric of layers 8, 9 and 10 is preferably a multifilament polyester fabric, which will promote the deposition and fixation of blood fibrin once the prosthesis and its branches or interconnecting prostheses have been installed and the anticoagulant effect of drugs which are administered to patients for this type of proceeding has been reversed.

In general terms, the concept of the invention is based on the fact that each of said layers 8, 9 and 10 has a very open fabric web and layers are concentric so as to overlap together to form a prosthesis wall or membrane which, between the webs of each layer, defines labyrinthine pores or interstices which are capable of keeping open for a predetermined time necessary for the tasks of implanting the prosthesis in the aorta and being sealed, as explained above, by fibrin from blood circulating through the aorta after said controlled time and once the complete prosthesis, with its arterial interconnections, has been implanted. Said pores are capable of being aligned by use of a tapered member, such as one end or tip of a balloon catheter or introducer dilator, which, upon passing through the web of each layer 8, 9, 10, forms an aperture or passage or channel 26 through wall 11 of prosthesis 1 that will allow to connect there a secondary interconnecting prosthesis 21 which is secured and sealed to the wall or membrane 11 of the prosthesis and into and against the involved collateral artery 13.

In other words, each layer 8, 9, 10, which forms the wall or membrane 11 of the main aortic prosthesis 1 has a physical structure or fabric which, once pierced by a non-cutting tapered member, allows the expansion of the pore being traversed to a desired or chosen diameter without breaking the fibers or yarns. This property is maintained throughout the extension of membrane 11 once the three layers 8, 9, 10 are radially expanded by the internal metal support or stent 2. The configuration of the cells of stent 2 once expanded, will allow the passage and fixation of the interconnecting prosthesis. Any of the cells may be radially deformed and will not limit the expansion of the interconnecting prosthesis 21 during its installation.

This will allow to pass through wall 11 of main prosthesis 1 and install the interconnecting prostheses or branches 21 in the exact locations in front of the chosen collateral arteries without the need to provide specific places of puncture, rupture, opening or interconnection on the main prosthesis as it happens in prosthetics of the prior art. This indeed the case, for example, in Bruszewsky's blouses and in the punchable patches of Cully et. al., both mentioned above in the prior art reference.

The invention may be better understood with reference to the following examples which are not limitative or restrictive of the scope of protection. On the contrary, it must be clearly understood that many other embodiments, modifications and alterations equivalent to the elements of the invention may be suggested by persons skilled in the art after reading the present description, without departing from the spirit of the present invention and/or the scope of the appended claims.

EXAMPLE

A prosthesis according to the invention was manufactured, the prosthesis comprised:

A closed cell type stent, made of stainless steel, of 47 mm in length, and with an expansion range of up to 40 mm in diameter, provided by the company Latecba S.A. similar to those used in SETA® endoprosthesis.

The liner was a tubular mesh arranged in a zig-zag pattern forming three concentric layers of knitting, jersey type. The tubular mesh was woven with multifilament polyester yarn textured in a straight double-needle machine with 20 needles per inch.

The liner was secured to the stent by Johnson & Johnson 4/0 Ethibond braided polyester sutures, disposed at both ends of the stent and aligned on the longitudinal axis. The liner had an initial diameter of 16 mm with a capacity to expand up to 30 mm.

The prosthesis also included two interconnecting prostheses made with Eucatech® expandable balloons renal stents covered with ultrafine PTFE membrane of SICBI G type from the company Latecba S.A from Argentina.

Figure 4:
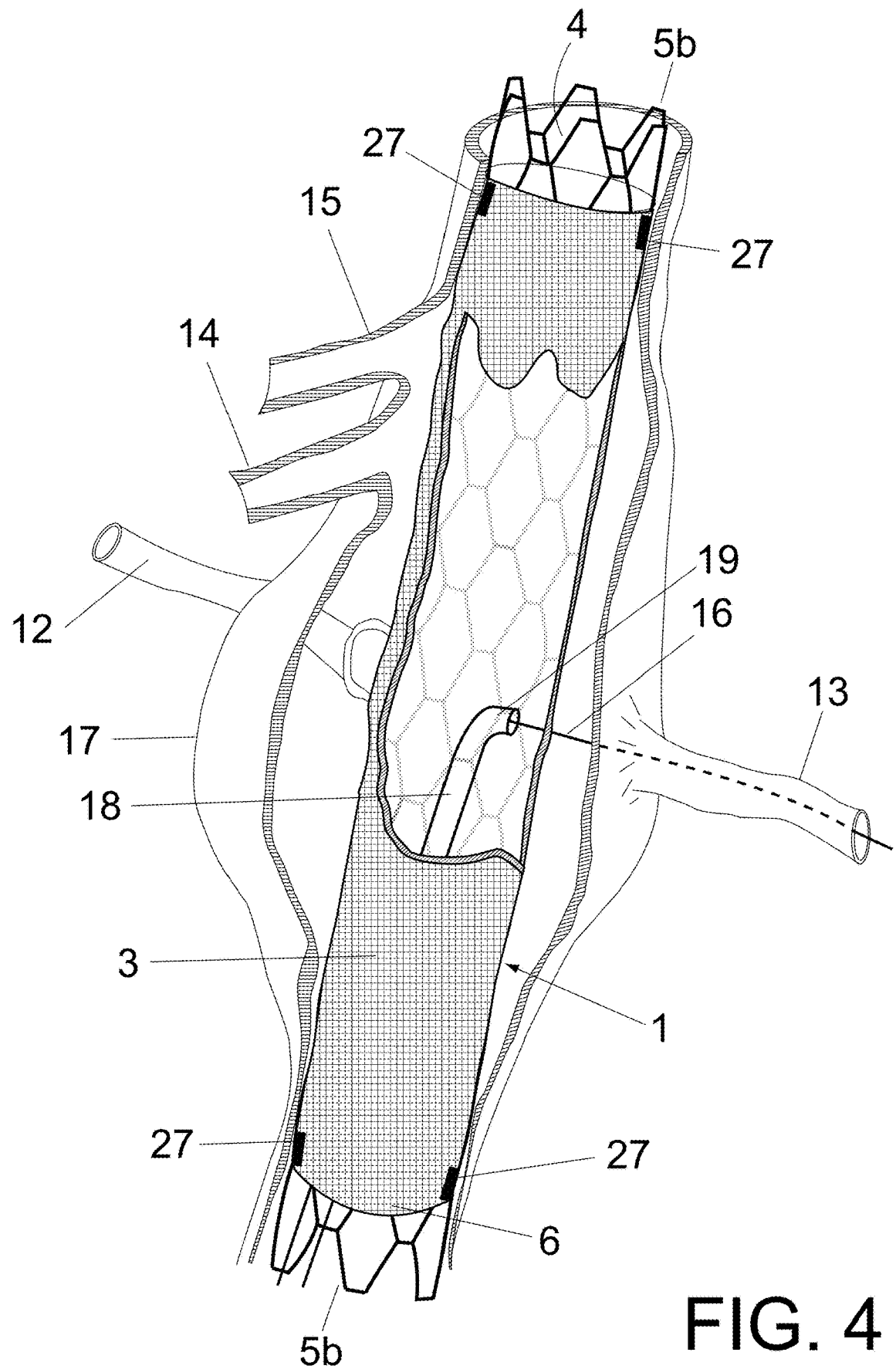
FIG. 4 shows an abdominal aorta bearing aneurysm, and the collateral arteries involved, i.e. the renal, superior mesenteric and celiac trunk, illustrating a main prosthesis of the invention already implanted and in a step prior to the implantation of the interconnecting prostheses for interconnecting collateral arteries, all in perspective and partially in section.

Referring now to the method proposed by the present invention, and in accordance with a first alternative thereof, main prosthesis 1 of the invention is positioned within the diseased section of the blood vessel, in this case the aorta, by means of a tubular positioning device such as a known first introducer, following any of the conventional hemodynamic procedures and obviously with the patient being properly heparinized, i.e. anti-coagulated. Once it is in the desired location where the prosthesis is to be implanted, for example in the aneurysm 17 shown in FIG. 4, main prosthesis 1 is released from the tubular positioning device leaving the prosthesis in position. The implant technique will depend on whether the main prosthesis is a balloon-expandable one or if it is self-expanding and in both cases the procedure known in the art will be followed. If the location to be treated is the abdominal aorta and the collateral arteries involved in the affected area are the renal arteries 12, 13, the superior mesenteric 14 and the celiac trunk 15, the prosthesis should extend above the celiac trunk and below the renal arteries, as shown an FIG. 4, wherein the prosthesis 1 is already installed and implanted. As can be seen, it does not matter that the prosthesis 1 extends over all of the collateral arteries 12 to 15 because, according to the invention, the ostia of these arteries are not occluded, that is to say it does not block their perfusion thanks to the open web of the fabric of each layer.

Both ends 4 and 6 of the prosthesis should be sealed in the proximal and distal necks of the lesion to be repaired. In order to correctly locate the ends of the aortic prosthesis of the invention, one or both ends may have contrast markers 27, see FIG. 1. Once the prosthesis has been deployed, there will proceed the detection of the location of each collateral artery to be connected using standard techniques of hemodynamic with catheters and contrast media to locate collateral arteries angiographically. This will be possible because of the high initial porosity of the membrane or wall 11 of prosthesis 1, in particular layers 8, 9 and 10, and the patient's anticoagulation state. That is, the blood flowing through prosthesis 1 once installed as shown, will pass through multi-layer wall 11 entering collateral arteries 12 to 15. Thus, with a contrast medium injected into the blood, the location of each artery to be connected will be detected with known angiography techniques. It is important to note that organs perfused by these collateral arteries will receive blood throughout the entire procedure, thus avoiding the undesirable consequences of partial and/or total and/or temporary and/or permanent obstructions. In this regard, it is noteworthy that all known prostheses are designed with mesh or membrane bearing impermeable or sufficiently closed webs to prevent any leakage of blood therethrough from the beginning. Because of this, if the prosthesis implanted in FIG. 4 had a membrane of those conventional in the art, the collateral arteries would be definitely occluded. If, in turn, said prosthesis of FIG. 4 had any of the membranes of the prior art and its installation were consuming or it were implanted incorrectly, temporarily or permanently occluded arteries would cause partial, total, temporary or permanent damage to the organs perfused by this collateral artery.

These temporary or permanent occlusions are not strange situations during the installation of any prosthesis. This usually occurs when the prosthesis is deployed in an incorrect place occluding one more collateral arteries. With a conventional prosthesis, immediate action should be taken to attempt to restore blood flow to the collateral involuntarily occluded. If this were to occur with the prosthesis of the present invention there would be no interruption of flow into the collateral artery. Specifically there would be no occlusion while the patient is under the effect of anticoagulants. In fact, the concept of the present invention is based on being able to install the aortic prosthesis extending along the aortic wall which includes the ostia of collateral arteries, without risk of lack of perfusion as passage of blood flow is guaranteed by the open web of fabric wall 11, composed of layers 8, 9, 10, for a desired and controllable period of time.

The flow through the mesh of the prosthesis of the invention is maintained while the patient is under the effects of anti-coagulation for the necessary time of the operation. Then, once the complete set of prostheses, including the interconnections with collateral arteries, has been installed and anti-coagulation has been reversed, the already explained effect of wall sealing will happen thanks to the deposit of the patient's blood fibrin on the novel net or web formed by layers 8, 9, 10 of wall 11.

Once the aortic prosthesis 1 has been installed, there will proceed sequentially the location of each of the collateral arteries to be preserved in order to connect them to the interior of the main prosthesis 1. For this purpose, the operator will have auxiliary devices known for hemodynamic techniques, among which we can mention: straight-ledge hydrophilic guides, retractable tip guide catheters, balloons, and introducers with dilator or mandrel. According to the invention, methods proposed for the connections of the interconnecting prostheses will be described below.

On the first guide (not shown) which was used to position and install the aortic prosthesis 1, a first valve introducer 18 with known dilator and retractable end 19 is advanced and positioned, at the level where the ostium of the artery to be connected has been detected. The dilator (not shown) of the introducer and said first guide are removed and the introducer is operated to bend retractable end 19 until facing it with the ostium of artery 13 to be connected which is located on the other side of membrane 11 of prosthesis 1, as shown in FIGS. 4 to 12. After verifying, by a new angiographic image, the correct positioning of first introducer 18, therein there will proceed advancing a straight tip second guide 16 until passing through the three layers of the membrane or wall 11 of prosthesis 1, entering inside collateral artery 13 to be connected, see FIG. 4. On second guide 16 which passes through the three layers of membrane 11 and which is already inside artery 13, a first catheter balloon 22 is advanced which will pass through the three layers 8, 9 and 10 of membrane 11 without difficulty, see FIG. 5. More particularly, tip 20 of first balloon 22 passes through interstices formed by the webs of the layers 8, 9 and 10 and is accommodated therein, displacing the strands or fibers of the webs of the uncut layers, without breaking or tearing such fibers or strands so as to form an open passage 26, from one side to the opposite side of prosthesis wall 1, as illustrated in FIGS. 5 to 12. By not cutting or tearing the fibers, there is no risk of future propagation of these tears as it occurs in the prior art which ends up breaking the mesh and generating unwanted leaks. This balloon 22, which should have a diameter smaller than the diameter of collateral artery 13 to be connected, is inflated to discipline and align interstices, holes or pores of the three layers 8, 9 and 10 through which second guide 16 passes. Then, it is deflated and removes the balloon leaving the holes of the three membranes 8, 9 and 10 oriented or partially aligned to facilitate the maneuvers of the next step.

Figure 7A:
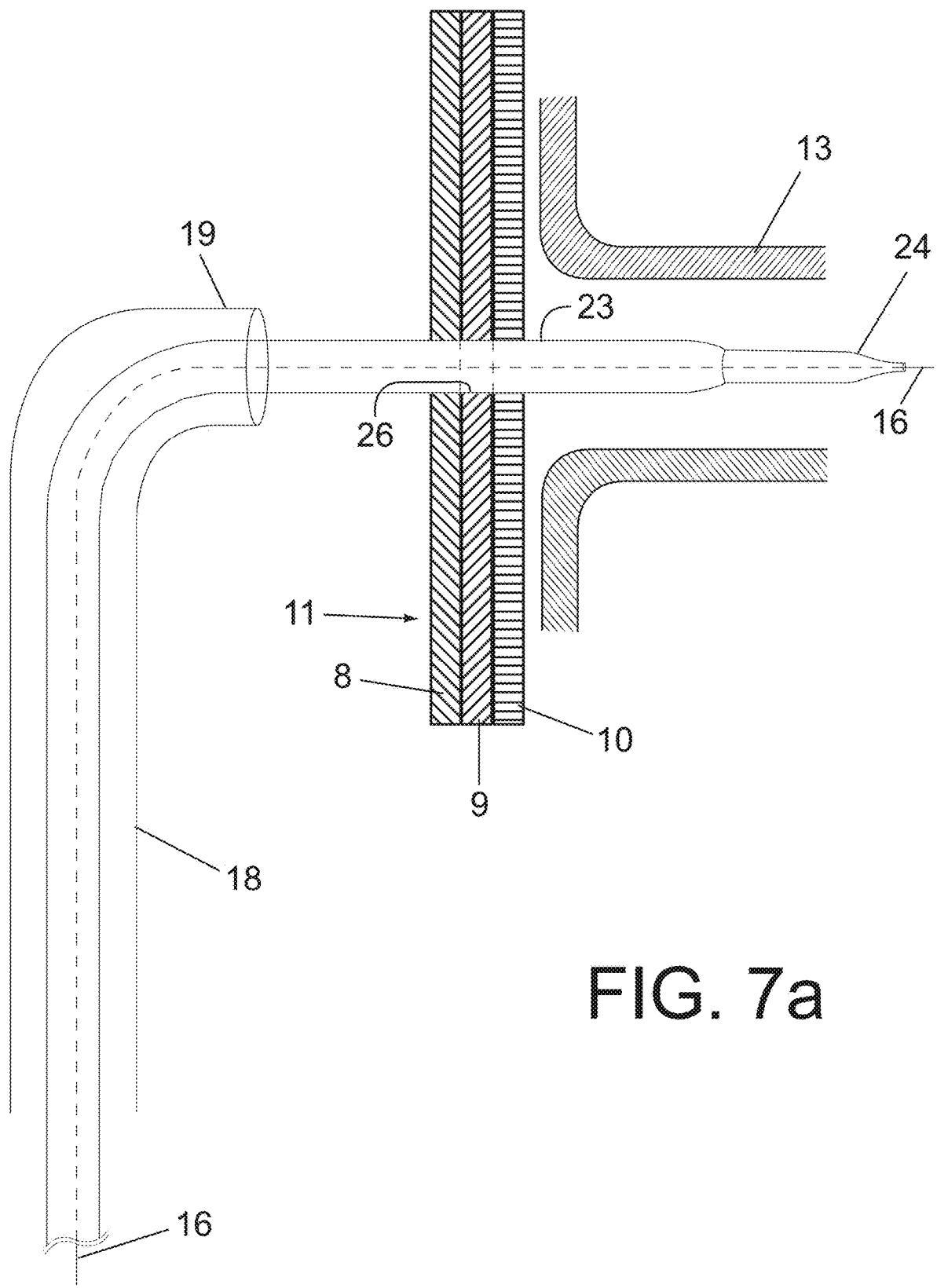
FIG. 7a shows a view similar to FIG. 6, wherein the balloon has been removed and a second introducer with dilator has been inserted into the artery to be connected.
Figure 8:
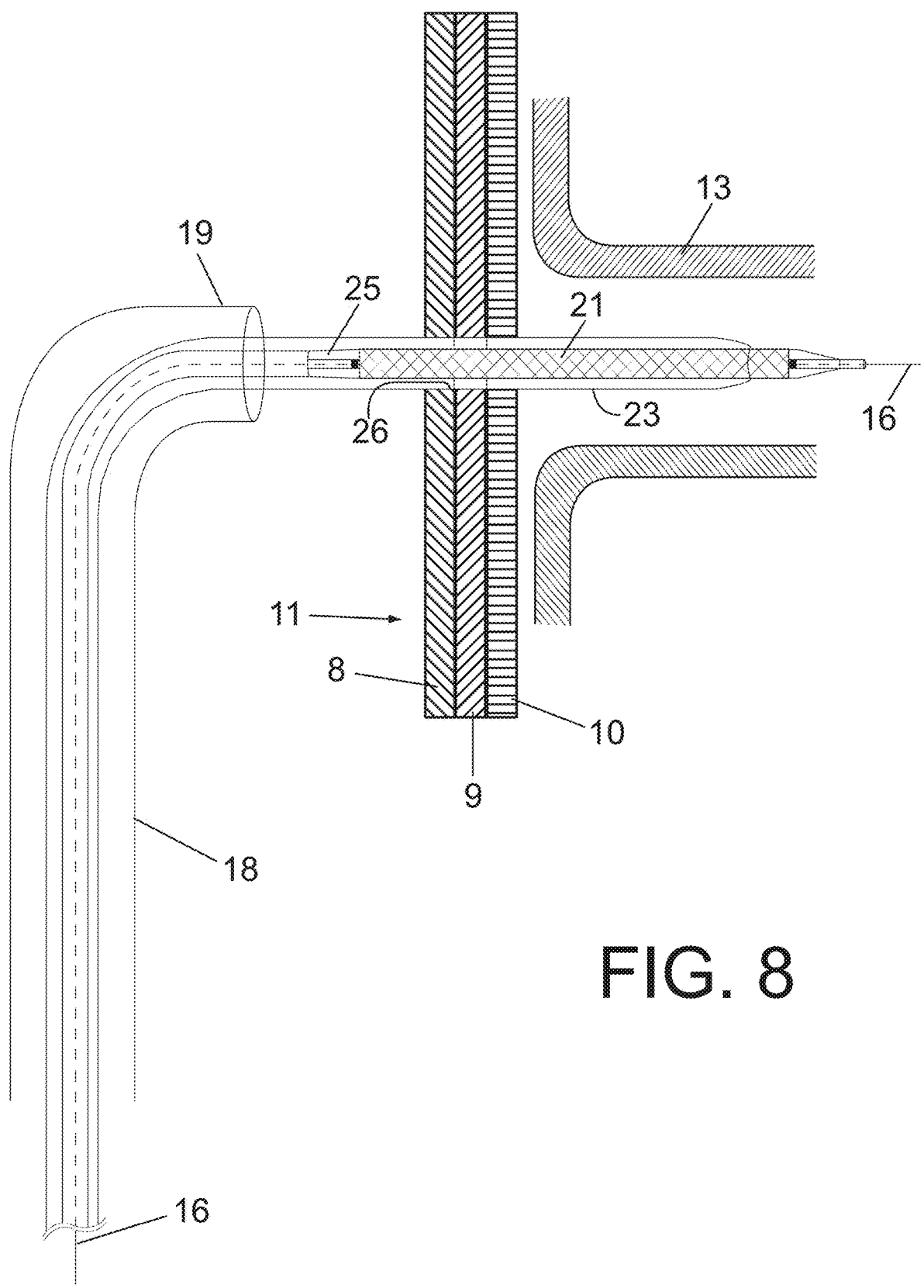
FIG. 8 shows a view similar to FIG. 7a where the dilator has been removed from the second introducer and it has been positioned inside the sheath of the second introducer, an interconnecting prosthesis being mounted on the expanding balloon partly within the artery to be connected and partially within the lumen of the main prosthesis, traversing the plurality of layers of the wall of the main prosthesis.
Figure 9:
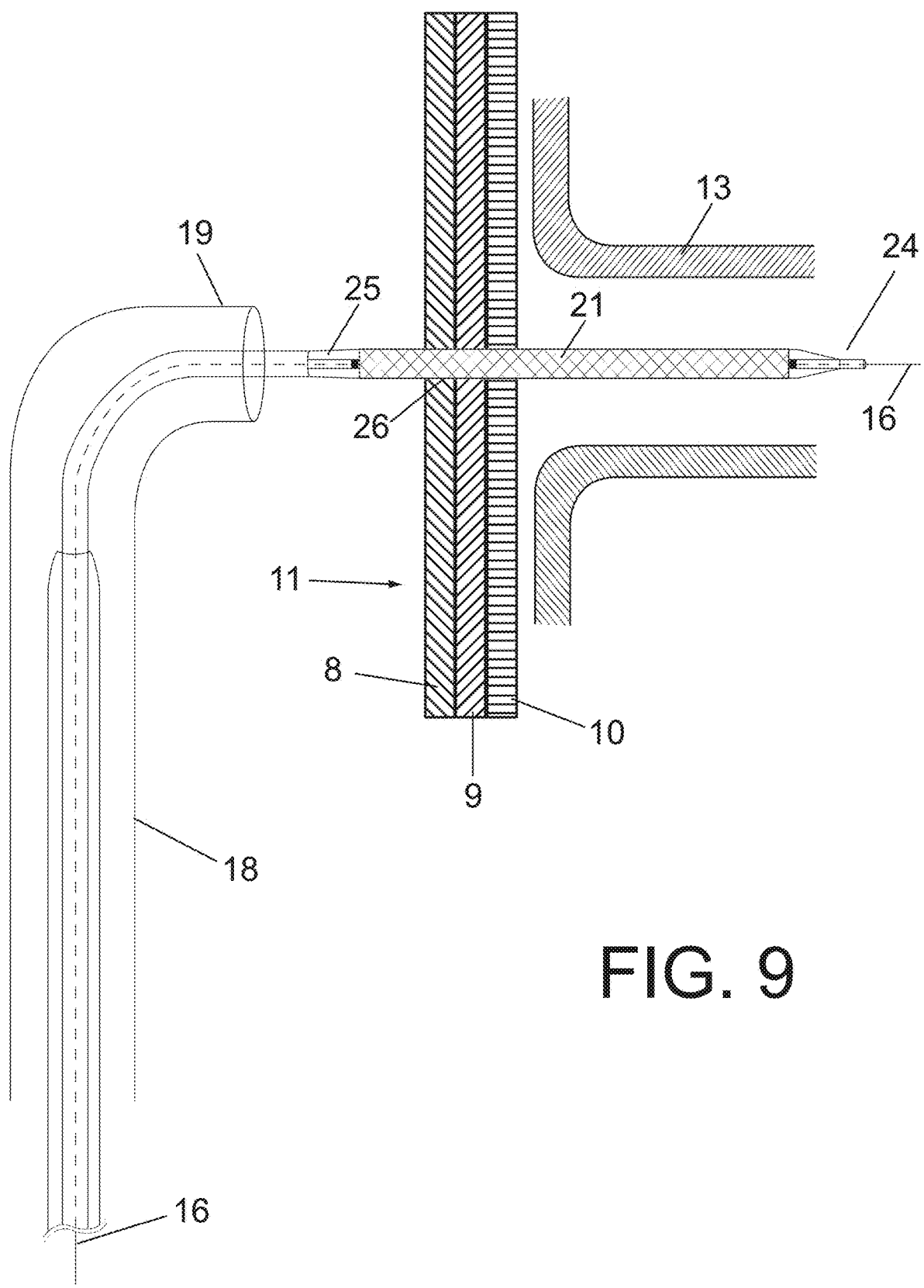
FIG. 9 shows a side view, partially in cross-section, of a step after the step of FIG. 8, wherein the sheath of the second introducer has been removed, with the interconnecting prosthesis, expandable balloon, being partially inserted into the renal artery to be connected and partially within the lumen of the main prosthesis, traversing the plurality of layers of the wall of the main prosthesis.

A second introducer 23 with a dilator or mandrel 24 which extends through the membrane through the aperture or passage 26 previously opened is advanced on the same second guide 16 and positioned within the collateral artery 13 to be connected, as shown in FIG. 7a. Then, dilator 24 is removed from this second introducer 23, and within the introducer, on second guide 16, interconnecting prosthesis 21, with its expanding balloon 25, advanced until positioning it in the desired location, as shown in FIG. 8. Once this location has been defined, second introducer is slid backwardly leaving branch or interconnecting prosthesis 21 in a condition of being expanded, as seen in FIG. 9. Balloon 25 of interconnecting prosthesis 21 is inflated, deploying it and dilating the opening or passage formed on the three layers and impacting the artery which is thus connected, see FIGS. 10 to 12.

As indicated above, first balloon 22 formed the aperture or passage 26 with a diameter smaller than the diameter of artery 13. This is so, because interconnecting prosthesis 21 must expand to the diameter of artery 13 to be implanted therein and, since this diameter is larger than the diameter of the passage 26, the prosthesis, by expanding beyond the diameter of passage 26, will generate a radial pressure sealing into passage 26 thus preventing future leakage, as finally seen installed in FIG. 12.

Figure 5:
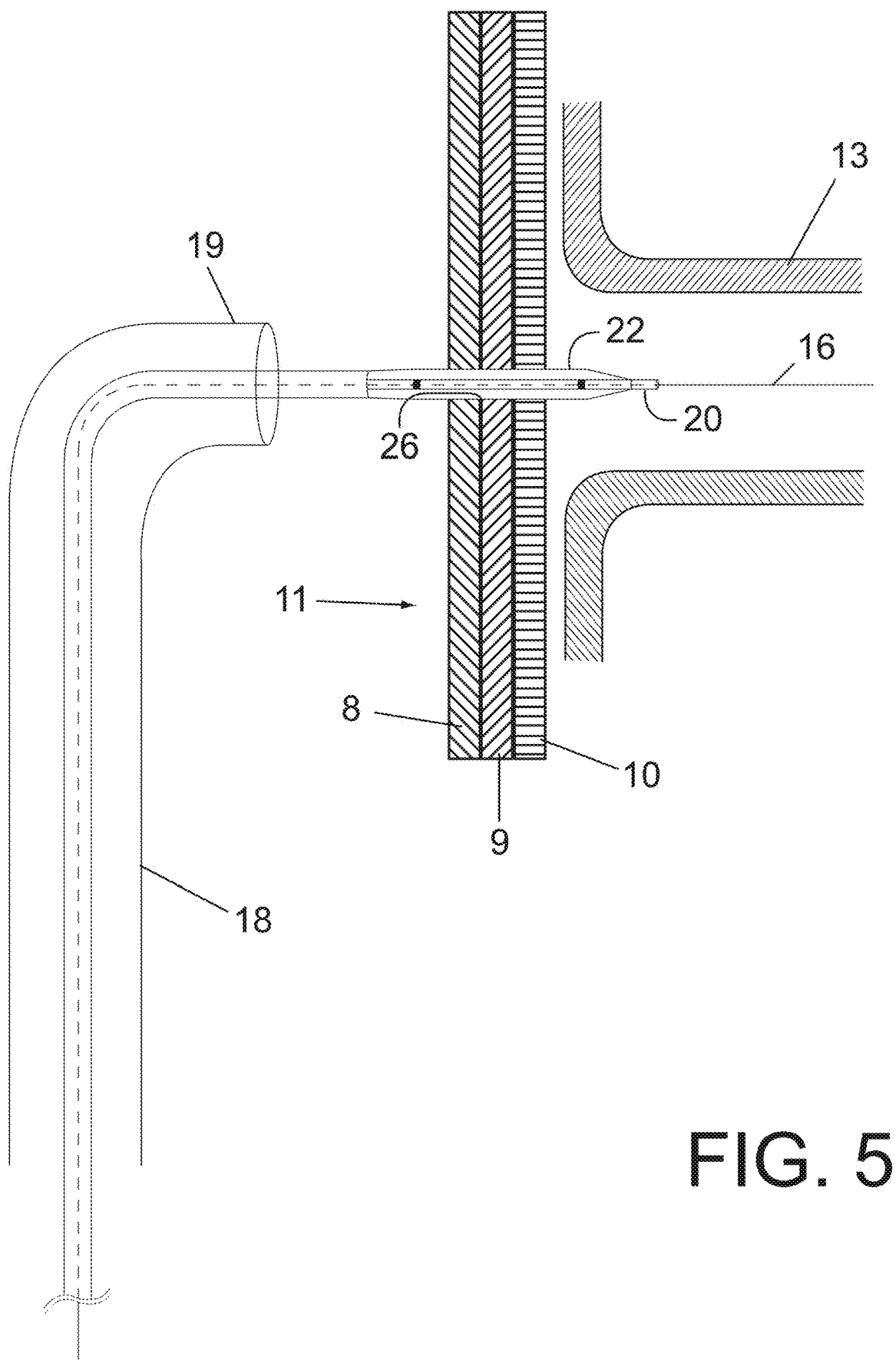
FIG. 5 shows a partial side elevation and cross-sectional view of a stage, or method step, prior to the implantation of an interconnecting prosthesis through the wall of the installed main prosthesis, wherein there can be seen a distal end of a balloon catheter through the multi-layer wall of the main prosthesis, in a section in front of the ostium of one of the renal arteries, by way of example.

According to a second alternative of the implanting method of the invention, it may not be necessary to use catheter balloon 22 which was employed to open the passage through layers 8, 9, 10, shown FIG. 5. In fact, said step for opening passage 26, shown in FIGS. 5 and 6, can be obviated and, instead, after having second guide 16 passing through wall 11 of the prosthesis, it is possible to advance on this second guide, second introducer 23 shown in FIG. 7a. Dilator 24 is then removed and the step illustrated in. FIGS. 8-12, already described above, is continued.

According to this second alternative, then, after installing the main prosthesis by endovascular route, using the first guide (not shown and well known in the art), first introducer 18, with valve and with dilator and retractable end, is advanced on said first guide. The dilator and said first guide are removed and retractable end 19 of the introducer is bent to face the ostium of a collateral vessel to be connected that is located on the other side of the wall of the main prosthesis, see FIG. 4. Then, the second straight tip guide 16 is advanced until said plurality of layers 8, 9, 10 of wall 11 of main prosthesis 1 are passed through, forming passage 26 through said wall. Second introducer 23, with a mandrel or dilator 24 mounted on second guide 16, is introduced and inserted with second guide 16 into collateral vessel 13, to be connected, through passage 26 open in layers 8, 9, 10 forming wall 11 and second introducer 23 with dilator 24 is positioned within collateral vessel 13 to be connected. Then it continues as in the first method as described, dilator 24 is then removed from second introducer 23 by inserting into second introducer 23 and onto second guide 16 an interconnecting prosthesis 21 mounted on an expanding balloon 25 and positioning the interconnecting prosthesis in the desired location, see FIG. 8. Then, second introducer 23 is slid backwardly to leave interconnecting prosthesis 21 in position within passage 26 and into collateral vessel 13 to be connected, see FIG. 9. Then, expanding balloon 25 is inflated with interconnecting prosthesis 21 mounted thereon, and interconnecting prosthesis is deployed, impacting it into passage 26 and into collateral vessel 13. Expanding balloon 25 is then deflated, removed together with second introducer 23, and first introducer 18 is positioned in the desired position to connect another collateral vessel, and the above steps for the connection of said other collateral vessel 12, 14 and 15 are thus repeated.

Figure 6:
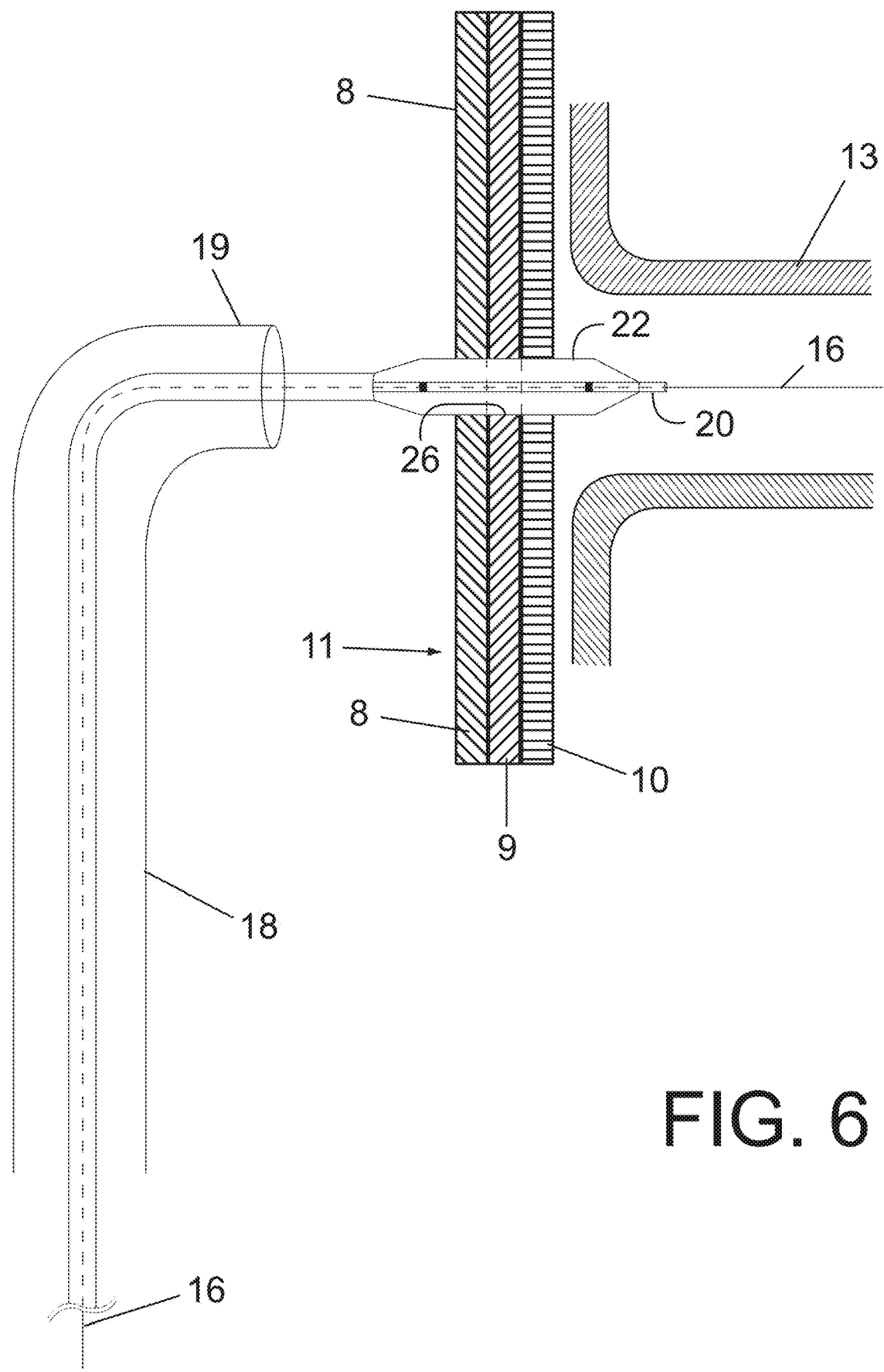
FIG. 6 shows a side view, partially in section, of a step after the stage or method step of FIG. 5, wherein the balloon is inflated to open a passage through the plurality of layers forming the wall of the main prosthesis.
Figure 7B:
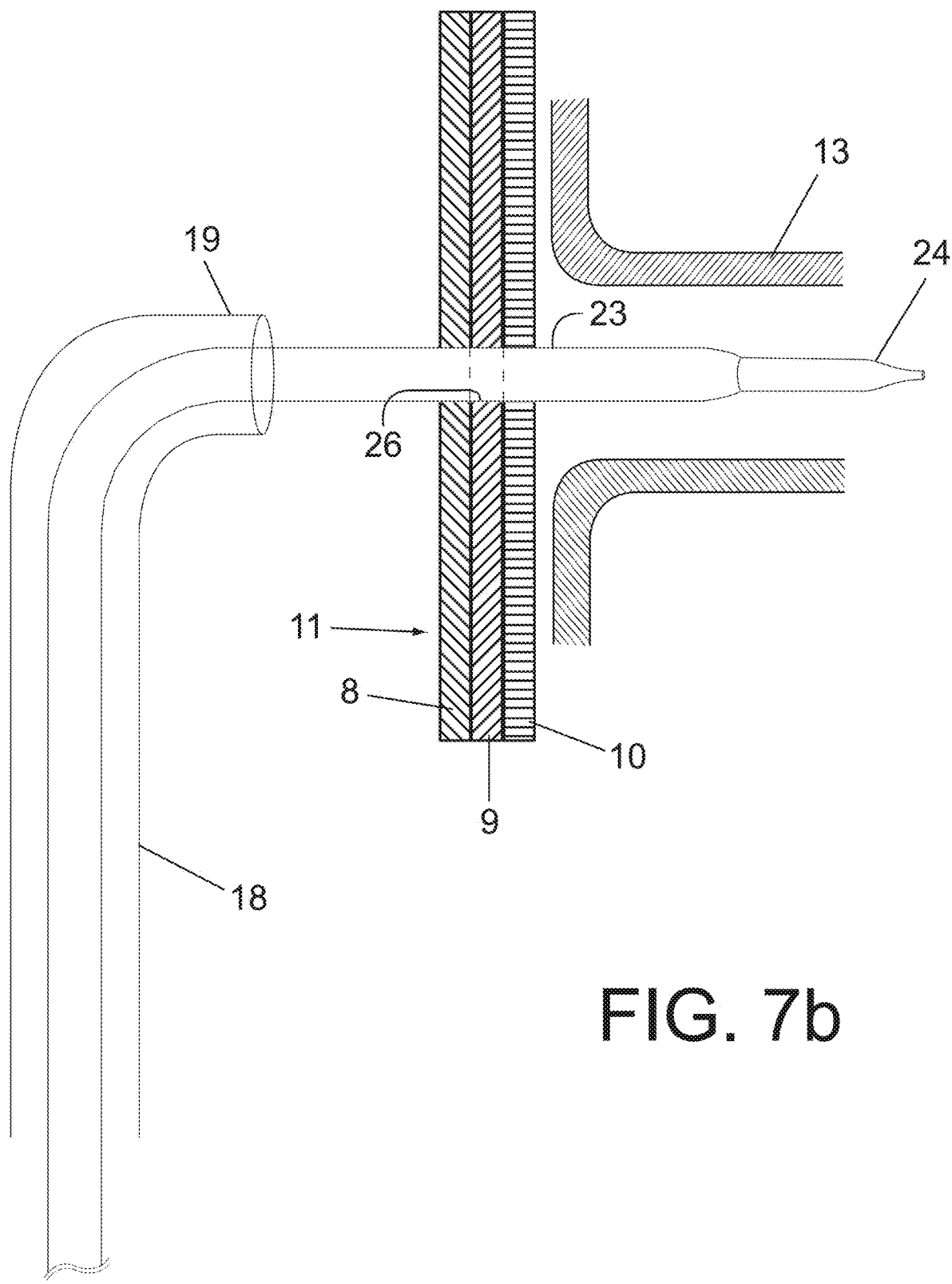
FIG. 7b shows a partial and cutaway side elevation view of a stage prior to the implantation of an interconnecting prosthesis through the wall of the installed main prosthesis, wherein the second introducer with its dilator can be seen, which has been introduced without the aid of a guide through the multi-layered wall of the main prosthesis and which is partially positioned within one of the renal arteries.

According to a third alternative of the implanting method of the invention, the use of the disciplining balloon 22, shown in FIGS. 5 and 6, can be suppressed by proceeding to pass through and control wall 11 and each of layers 8, 9, 10, by using introducer 23 with dilator 24, see FIG. 7b. Introducer with its dilator 24 is introduced and advanced, without assistance of second guide 16 (not used in this case) inside first introducer 18. By exerting a slight rotation on the axis of second introducer 23 with its dilator 29 and pushing forward, the plurality of layers 8, 9, 10 forming wall 11 of main prosthesis 1 are passed through, thus generating passage 26 through it and positioning second introducer 23 with its dilator 24 into the collateral vessel to connected 13. Once the plurality of layers 8, 9, 10 are passed through, second guide 16 is positioned through dilator 24 of introducer 23 into the collateral artery to be connected 13, continuing with the steps indicated in the other alternatives to proceed with the illustrated steps in FIGS. 8 to 12.

Figure 10:
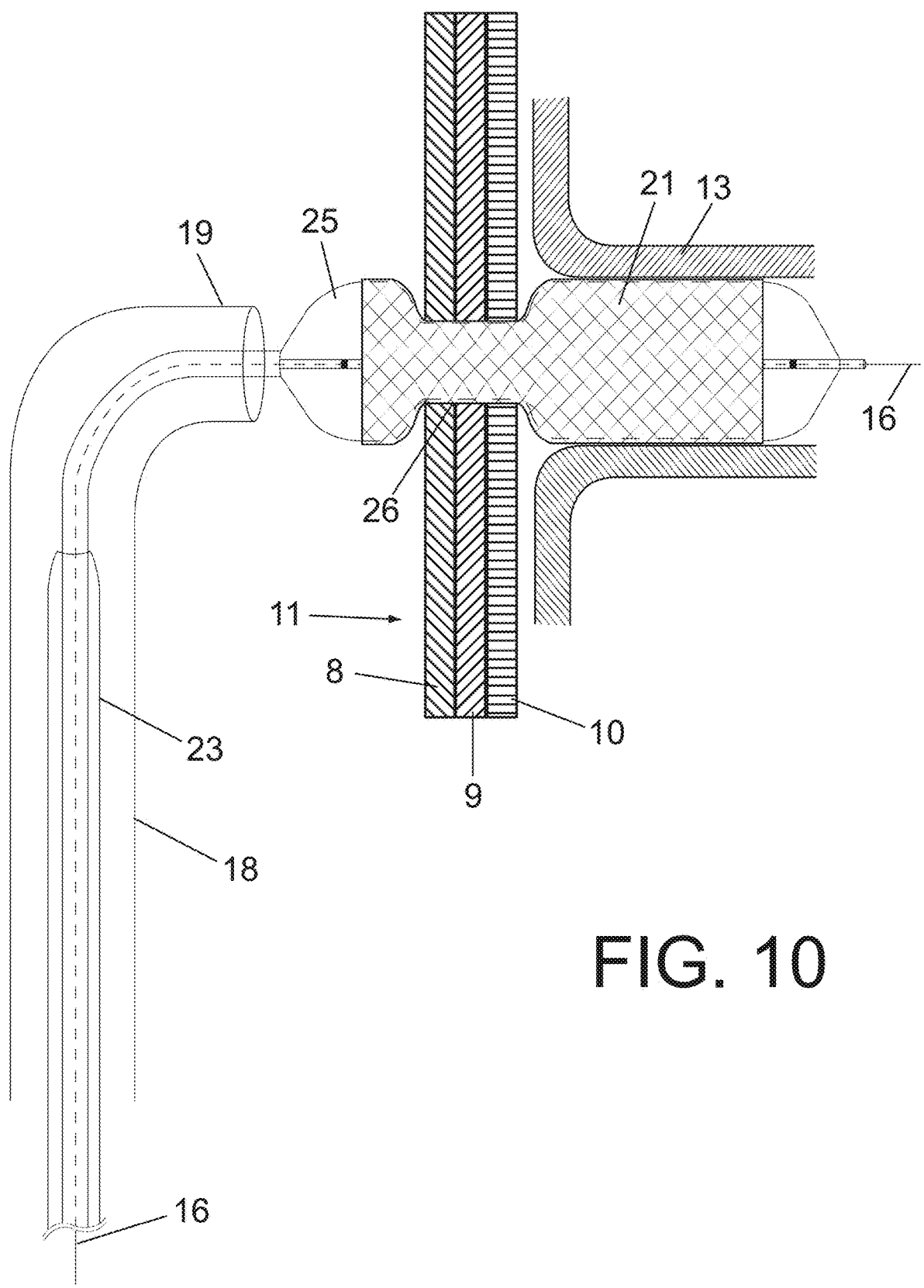
FIG. 10 shows a side elevation view, partially in cross-section, of a step after the step of FIG. 9, wherein an expanding balloon of the prosthesis inflated and expanded to anchor the interconnecting prosthesis to the wall of the main aortic prosthesis and within the renal artery.
Figure 11:
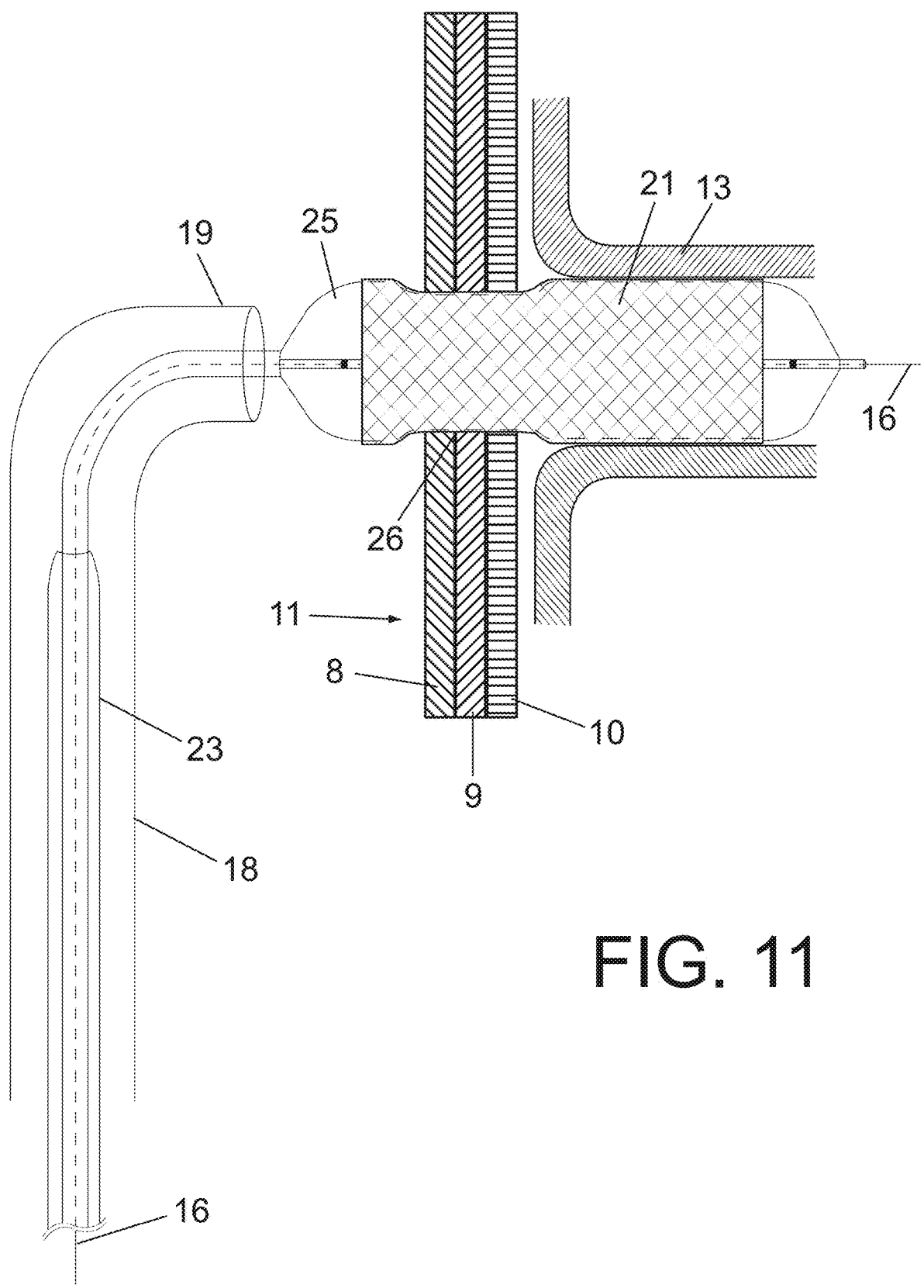
FIG. 11 shows a view similar to FIG. 10, wherein the expanding balloon has expanded the interconnecting prosthesis to its final expansion diameter.
Figure 12:
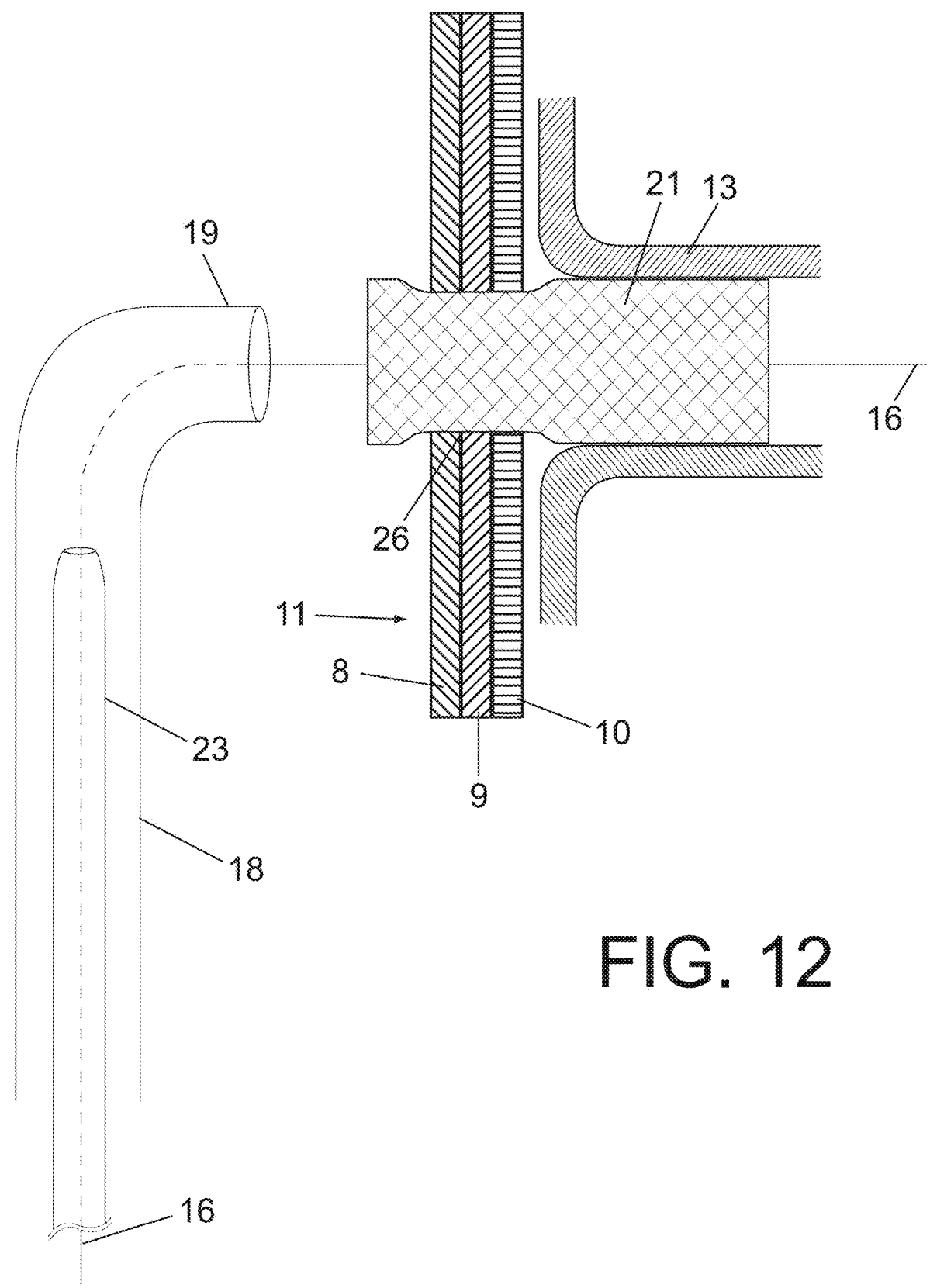
FIG. 12 shows a view similar to FIG. 11, wherein the expanding balloon has been removed while the interconnecting prosthesis is in place.

Subsequently, once artery 13 has been connected, as shown in FIGS. 10-12, and in accordance with any of the alternatives described above, balloon 25, which was used to expand interconnecting prosthesis 21, is removed and introducer 18 is positioned in another artery to be connected, repeating the same steps as carried out to interconnect artery 13.

The secondary or interconnecting prosthesis 21 may comprise a lined stent which is well known in the art and which, for such reasons, will not be described in detail.

Finally, all collateral arteries are in fluid communication with the interior of main prosthesis 1, allowing the passage of blood flow without any inconvenience and also, successfully isolating the diseased section such as aneurysm and/or abdominal dissection. The implantation of interconnecting prosthesis in all collateral arteries can take the time necessary to complete the implant or installation without risk of lack of perfusion of each of the collateral arteries during the procedure. Indeed, as long as the patient anti-coagulated, blood will continue to pass through wall 11 reaching arteries 12, 13, 14, 15, which have not yet been interconnected. Once all the collateral arteries have been interconnected and the anticoagulant effect in the patient has been dissipated, fibrin of blood begins to deposit on the three-dimensional labyrinthine web formed by the three webs or fabrics of layers 8, 9 and 10, sealing the pores and interstices. This three-dimensionality and labyrinthine design is what allows the deposit and fixation of fibrin that covers the wall of the prosthesis by sealing it and preventing the passage of blood into the aneurysmal sac.

As can be seen, the present invention focuses on a main prosthesis comprising a support and a liner constituted by at least two or three concentric layers that are overlapped with each other. By arranging such layers of a very open fabric web, the temporal passage of blood flow from the aorta to the respective arteries, as mentioned above, is allowed. This provides longer intervention times on the patient, thus avoiding possible risks for the patient.

Unlike conventional prosthesis and prosthesis from the prior art cited above, the present invention, as clearly described and illustrated above, consists of a support lined by a plurality of concentric layers of an expandable fabric having a web sufficiently open to permit passage of interconnecting prosthesis through all the layers and its fixation and sealing in said layers without being necessary to break meshes of each layer. The web of meshes of the different layers is also sufficiently open so that during the implantation of the prosthesis in the patient, who is anti-coagulated, blood flow to the corresponding collateral arteries is guaranteed, giving the operator time necessary to complete the implantation of the corresponding prosthesis that will connect the interior of the prosthesis implanted with the collateral arteries, all without the need to "break" the liner or coating of the prosthesis. Once the implantation of the collateral branches is completed and the anticoagulant effect has been reversed, the process of fibrin fixation on and between the different fabric layers begins, forming a three-dimensional blood impermeable matrix excluding aneurysm from blood circulation.

While preferred embodiments of the present invention have been illustrated and described, it will be obvious to those skilled in the art that various changes and modifications may be made therein without departing from the scope of the invention as defined in the appended claims.

I claim:

1. A prosthesis for repairing a main blood vessel having at least one collateral blood vessel branching therefrom by intraluminal insertion and fixation, for insertion into the main blood vessel of a patient for covering a diseased section of the main blood vessel, the prosthesis comprising:

(a) at least one expandable collateral vessel prosthesis having a third outer diameter in its expanded state for contacting an interior wall of a collateral blood vessel, and
(b) a main prosthesis consisting of:
  (i) an expandable support for firmly affixing into said main blood vessel and along said diseased section, the expandable support comprising in an expanded state a plurality of cells having an expanded configuration that is deformable to permit passage through the expandable support of the least one collateral vessel prosthesis, and
  (ii) a liner in the form of a tube having two opposing ends and a middle portion longitudinally between the ends, the liner consisting of a plurality of adjacent, concentric layers being overlapped together and in intimate contact with each other to form a three-dimensional matrix constituting a wall, each of said layers comprising a knitted fabric of displaceable fibers in the form of an open web, the webs of each of said overlapped layers forming labyrinthine interstices in the three-dimensional matrix between adjacent layers, the concentric layers being independent of each other at least in the middle portion of the liner,
the liner having a first initial water porosity of more than 2500 cm3/cm2/minute,
the labyrinthine interstices having a first, initial diameter and being radially alignable and expandable to a second internal diameter up to a size to permit the expandable collateral prothesis to expand to the third outer diameter, without cutting or breaking of the fibers so as to permit formation of a passage through the wall so as to accommodate therethrough said collateral vessel prosthesis, and
wherein each layer on its own has a second porosity greater than the first porosity.

2. The prosthesis of claim 1, wherein said expandable support is at least one stent extending all along the liner and extending beyond each of the two opposing ends of the liner to form anchor portions for anchoring against a wall of the blood vessel.

3. The prosthesis of claim 2, wherein said stent is selected from the group consisting of a balloon-expandable stent and a self-expanding stent.

4. The prosthesis of claim 1, wherein each layer has the same second porosity.

5. The prosthesis of claim 1, wherein each layer provides a porosity and the porosity of each layer is different from the porosity of the other layers.

6. The prosthesis of claim 1, wherein the layers are made of the same fabric material.

7. The prosthesis of claim 1, wherein the layers are made of different fabric material.

8. The prosthesis of claim 1, wherein the fabric material is selected from the group consisting of a knitted web and a warp and weft fabric.

9. The prosthesis of claim 1, wherein the plurality of layers forming the wall of the main prosthesis comprises a continuous fabric invaginated into a zig-zag pattern.

10. The prosthesis of claim 1, wherein the plurality of layers forming the wall of the main prosthesis is formed of independent fabric materials.

11. The prosthesis of claim 1, wherein the plurality of layers comprises at least two layers.

12. The prosthesis according to claim 1, wherein the liner consists of a single piece of knitted fabric which is folded back on itself at one or both of the two opposing ends.

13. The prosthesis according to claim 1, wherein the liner consists of separate pieces of knitted fabric which are not connected at the two opposing ends.

* * * * *